(12) United States Patent
Goldin et al.

(10) Patent No.: US 6,569,160 B1
(45) Date of Patent: May 27, 2003

(54) SYSTEM AND METHOD FOR DETECTING ELECTRODE-TISSUE CONTACT

(75) Inventors: Alexander Goldin, Haifa (IL); Michael Levin, Haifa (IL); Avraham Matcovitch, Nesher (IL)

(73) Assignee: Biosense, Inc., New Brunswick, NJ (US)

( * ) Notice: Subject to any disclaimer, the term of this patent is extended or adjusted under 35 U.S.C. 154(b) by 353 days.

(21) Appl. No.: 09/612,606

(22) Filed: Jul. 7, 2000

(51) Int. Cl.[7] .................................. A61B 18/18

(52) U.S. Cl. ........................ 606/41; 606/34; 606/49; 600/427

(58) Field of Search .................. 606/32, 39, 38, 606/41, 42, 49; 600/374, 375, 427, 378, 424; 607/119, 122, 101

(56) References Cited

U.S. PATENT DOCUMENTS

| | | |
|---|---|---|
| 4,532,924 A | 8/1985 | Auth et al. ............ 128/303.17 |
| 4,605,897 A | 8/1986 | Gelinas |
| 4,682,596 A | 7/1987 | Bales et al. ............ 128/303.14 |
| 4,771,237 A | 9/1988 | Daley |
| 4,852,580 A | 8/1989 | Wood ........................ 128/693 |
| 4,945,912 A | 8/1990 | Langberg ................... 128/642 |
| 4,966,597 A | 10/1990 | Cosman ....................... 606/50 |
| 5,078,714 A | 1/1992 | Katims ........................ 606/38 |
| 5,274,328 A | 12/1993 | Begin et al. |
| 5,282,840 A | 2/1994 | Hudrlik ....................... 607/28 |
| 5,341,807 A | 8/1994 | Nardella ..................... 128/642 |
| 5,409,000 A | 4/1995 | Imran ........................ 128/642 |
| 5,419,767 A | 5/1995 | Eggers et al. ............... 604/114 |
| 5,447,529 A | 9/1995 | Marchlinski et al. ......... 607/99 |
| 5,454,809 A | 10/1995 | Janssen ....................... 606/41 |
| 5,469,857 A | 11/1995 | Laurent et al. ............. 128/710 |
| 5,494,042 A | 2/1996 | Panescu et al. ......... 128/695 R |
| 5,546,951 A | 8/1996 | Ben-Haim ................. 128/702 |
| 5,553,611 A | 9/1996 | Budd et al. |
| 5,562,721 A | 10/1996 | Marchlinski et al. ......... 607/99 |
| 5,577,509 A | 11/1996 | Panescu et al. ............. 128/696 |
| 5,598,848 A | 2/1997 | Swanson et al. ............. 128/696 |
| 5,626,576 A | 5/1997 | Janssen ....................... 606/41 |
| 5,629,621 A | 5/1997 | Goldfine et al. |
| 5,644,229 A | 7/1997 | Dossel et al. |
| 5,662,108 A | 9/1997 | Budd et al. .................. 128/642 |
| 5,673,704 A | 10/1997 | Marchlinski et al. ....... 128/739 |
| 5,718,241 A | 2/1998 | Ben-Haim et al. ........... 128/702 |
| 5,722,402 A * | 3/1998 | Swanson et al. ............ 607/122 |
| 5,738,096 A | 4/1998 | Ben-Haim ................ 128/653.1 |

(List continued on next page.)

FOREIGN PATENT DOCUMENTS

| | | |
|---|---|---|
| EP | 158 298 | 10/1985 |
| EP | WO 97 04702 A | 2/1997 |
| EP | 0 928 601 | 7/1999 |

(List continued on next page.)

OTHER PUBLICATIONS

European Search Report dated Oct. 10, 2001.
European Search Report, No. 01305873.0 Dated Nov. 10, 2001.

(List continued on next page.)

*Primary Examiner*—Linda C. M. Dvorak
*Assistant Examiner*—David M. Ruddy
(74) *Attorney, Agent, or Firm*—Louis J. Capezzuto; Frederick L. Herman

(57) ABSTRACT

A system for detecting electrode-tissue contact comprises a catheter having a location sensor and a distal tip electrode. The catheter preferably further comprises a reference electrode that is preferably protected from making contact with tissue. The system further comprises a signal generator to transmit test signals to the distal tip and reference electrodes. Tissue contact is detected by comparing the signals across the tip electrode to a return electrode versus the signal across the reference electrode to a return electrode. Ablation energy may be delivered to the distal tip electrode if contact of the electrode with tissue is detected.

57 Claims, 15 Drawing Sheets

U.S. PATENT DOCUMENTS

| | | | |
|---|---|---|---|
| 5,749,914 A | 5/1998 | Janssen | 607/116 |
| 5,792,185 A | 8/1998 | Burton et al. | 607/2 |
| 5,833,621 A | 11/1998 | Panescu et al. | 600/509 |
| 5,836,874 A | 11/1998 | Swanson et al. | 600/374 |
| 5,836,875 A | 11/1998 | Webster, Jr. | 600/374 |
| 5,836,990 A | 11/1998 | Li | 607/28 |
| 5,891,095 A | 4/1999 | Eggers et al. | 604/114 |
| 5,899,860 A | 5/1999 | Pfeiffer et al. | |
| 5,916,158 A | 6/1999 | Webster, Jr. | |
| 5,935,079 A | 8/1999 | Swanson et al. | 600/509 |
| 5,944,022 A | 8/1999 | Nardella et al. | 128/899 |
| 6,064,905 A | 5/2000 | Webster, Jr. et al. | 600/424 |
| 6,183,468 B1 * | 2/2001 | Swanson et al. | 606/34 |
| 6,241,724 B1 * | 6/2001 | Fleischman et al. | 606/41 |
| 6,264,653 B1 * | 7/2001 | Falwell | 606/41 |

FOREIGN PATENT DOCUMENTS

| | | |
|---|---|---|
| EP | 0 965 302 A2 | 12/1999 |
| EP | 1 005 838 A1 | 6/2000 |
| JP | 10094609 | 4/1998 |
| WO | WO 90/07303 | 7/1990 |
| WO | WO 94/00050 | 1/1994 |
| WO | WO 96/05768 | 2/1996 |
| WO | WO 97/12548 | 4/1997 |
| WO | WO 97/24981 A2 | 7/1997 |
| WO | WO 97/24981 A3 | 7/1997 |
| WO | WO 97 29678 A | 8/1997 |
| WO | WO 97/29701 | 8/1997 |
| WO | WO 98/43547 | 10/1998 |
| WO | WO 99/05971 | 2/1999 |
| WO | WO 99/39650 | 8/1999 |
| WO | WO 99/52430 | 10/1999 |
| WO | WO 00/15130 A3 | 3/2000 |
| WO | WO 00/15130 A2 | 3/2000 |
| WO | WO 00 16705 A | 3/2000 |
| WO | WO 00 78239 A | 12/2000 |

OTHER PUBLICATIONS

Pallas–Areny, Ramon; Webster, John G.; Bioelectric Impedance Measurements Using Synchronous Sampling: IEEE Transactions on Biomedical Engineering, vol. 40, No. 8 Aug. 1993; pp 824–829.

Promotional Brochure for TaCCor Catheter Ablation System; taCCor, Inc., 1837 Kempton Rd., Charleston, SC; 2 pp.

Plonsey, Robert; Barr, Roger C.; A Critique of Impedance Measurements in Cardiac Tissue; Annals of Biomedical Engineering, vol. 14, 1986; pp. 307–322.

Rush, Stanley, Ph.D.; Abildskov, J.A., M.D.; McFee, Richard, Ph.D.; Resistivity of Body Tissues at Low Frequencies; Circulation Research, vol. XII, Jan. 1963; pp 40–50.

Panescu, Dorin; Whayne, James G.; Fleischman, Sidney D.; Mirotznik, Mark S.; Swanson, David K.; Webster, John G.; Three–Dimensional Finite Element Analysis of Current Density and Temperature Distributions During Radio–Frequency Ablation; IEEE Transactions on Biomedical Engineering, vol. 42, No. 9, Sep. 1995; pp 879–890.

* cited by examiner

SYSTEM AND METHOD FOR DETECTING ELECTRODE-TISSUE CONTACT

FIELD OF THE INVENTION

The present invention is directed to a system and method for detecting contact of an electrode with tissue. The system and method of the invention are particularly suited for use in conjunction with intracardiac electrophysiology or electromechanical studies or in conjunction with therapeutic procedures such as cardiac ablation.

BACKGROUND OF THE INVENTION

Cardiac arrhythmias, the most common of which is ventricular tachycardia (VT), are a leading cause of death. In a majority of patients, VT originates from a 1 mm to 2 mm lesion located close to the inner surface of the heart chamber. One of the treatments for VT comprises mapping the electrical pathways of the heart to locate the lesion followed by ablation of the active site.

Commonly assigned U.S. Pat. No. 5,546,951; U.S. patent application Ser. No. 08/793,371; and PCT application WO 96/05768, which are incorporated herein in their entirety by reference, disclose methods for sensing an electrical property of heart tissue such as local activation time as a function of the precise location within the heart. The data are acquired by advancing into the heart one or more catheters that have electrical and location sensors in their distal tips. The precise three-dimensional location of the catheter tip is ascertained by the location sensor contained therein. The location sensor operates by generating signals that are responsive to its precise location within an externally generated non-ionizing field such as an electromagnetic field. Simultaneous with the acquisition of location information, electrical information is also acquired by at least one electrode contained at the catheter distal tip. Accurate sensing of location and electrical information by sensors contained in the catheter generally requires a high degree of confidence that a catheter electrode is in contact with the tissue.

In systems that use acoustic means to determine the location of mapping and ablation electrodes, it is likewise important to determine that the electrodes are in contact with the tissue to be mapped or ablated. For example, U.S. Pat. No. 5,409,000, the disclosure of which is incorporated herein in its entirety by reference, discloses the use of a catheter probe having a plurality of flexible, longitudinally extending circumferentially spaced apart arms adapted to be disposed within a chamber of a heart. Electrodes are carried by the arms and are adapted to be moved into engagement with the wall of the heart. Markers visible ultrasonically are carried by the arms for encoding the arms so that one arm can be distinguished from another. An ablation catheter having ultrasonic viewing means such as an ultrasonic sensor or transducer at its distal extremity is carried by and is slidably mounted in the catheter probe. The distal extremity of the ablation catheter is moveable into positions to view ultrasonically the markers carried by the arms of the catheter probe so that the arms can be identified and the spacing of the arms can be ascertained.

PCT application WO 99/05971, the disclosure of which is incorporated herein in its entirety by reference, discloses a system that uses one or more ultrasound reference catheters to establish a fixed, three-dimensional coordinate system within a patient's heart using principles of triangulation. The coordinate system is represented graphically in three dimensions on a video monitor and is reported to aid the clinician in guiding other medical devices, which are provided with ultrasound sensors or transducers, through the body to locations at which they are needed to perform clinical procedures. The system is reported to be useful to help a physician guide mapping catheters for measuring electrical activity and ablation catheters for ablating selected regions of cardiac tissue, to desired locations within the heart.

Methods of creating a map of the electrical activity of the heart based on these data are disclosed in commonly assigned U.S. patent application Ser. Nos. 09/122,137 and 09/357,559 filed on Jul. 24, 1998 and Jul. 22, 1999, respectively, and in European Patent Application 974,936 which are also incorporated herein in their entirety by reference. In clinical settings, it is not uncommon to accumulate data at 100 or more sites within the heart to generate a detailed, comprehensive map of heart chamber electrical activity. The use of the location sensors as hereinabove described is highly useful in providing a detailed and accurate map of the heart chamber's activity.

Catheters containing position or location sensors may also be used to determine the trajectory of points on the cardiac surface. These trajectories may be used to infer mechanical motion characteristics such as the contractility of the tissue. As disclosed in U.S. Pat. No. 5,738,096 which is incorporated herein in its entirety by reference, maps depicting such motion characteristics, which may be superimposed with maps depicting local electrical information, may be constructed when the trajectory information is sampled at a sufficient number of points in the heart. Accurate maps of such motion characteristics again require confidence that the data are acquired when the catheter tip is in contact with the cardiac tissue.

The detailed maps generated as hereinabove described may serve as the basis for deciding on a therapeutic course of action, for example, tissue ablation, to alter the propagation of the heart's electrical activity and to restore normal heart rhythm. In cardiac ablation, energy, typically in the radiofrequency (RF) range, is supplied at selected points on the intracardiac surface by a catheter having an ablation electrode at its distal tip. Ablation is effected by bringing the distal tip electrode into contact with the locus of aberrant electrical activity and by initiating the delivery of RF energy through the distal tip electrode from an external RF generator in communication with the distal tip electrode. Ablation is most effectively performed when the distal tip electrode is in contact with the cardiac wall. Absence of contact or poor contact of the tip electrode with the heart wall leads to dissipation of the RF energy in the blood, as well as possible fouling of the tip electrode with the concomitant possibility of blood clot formation. Accordingly, it is important that both mapping and ablation be accompanied by methods and systems for detecting and ensuring electrode-tissue contact.

A number of references have reported methods to determine electrode-tissue contact, including U.S. Pat. Nos. 5,935,079; 5,891,095; 5,836,990; 5,836,874; 5,673,704; 5,662,108; 5,469,857; 5,447,529; 5,341,807; 5,078,714; and Canadian Patent Application 2,285,342. A number of these references, e.g., U.S. Pat. Nos. 5,935,079, 5,836,990, and 5,447,529 determine electrode-tissue contact by measuring the impedance between the tip electrode and a return electrode. As disclosed in the '529 patent, it is generally known that impedance through blood is generally lower that impedance through tissue. Accordingly, tissue contact has been detected by comparing the impedance values across a set of electrodes to pre-measured impedance values when an electrode is known to be in contact with tissue and when it is known to be in contact only with blood. A problem in using this method during intracardiac procedures is the fact that tissue and blood impedances may change during a procedure. Furthermore, the impedance through tissue also depends on the state of the tissue. For instance, impedance through infarcted tissue is known to be less than the impedance through healthy tissue.

U.S. Pat. No. 5,341,807 discloses a method of detecting contact of a catheter tip electrode with tissue. The method of the '807 patent employs a catheter having a tip electrode and a plurality of axially spaced ring electrodes mounted along the catheter surface. A test signal is applied across a pair of outer electrodes arranged along the catheter. Each outer electrode is paired with an inner electrode to develop a sensing signal characteristic of impedance for the tissue between the electrodes. One major drawback to the catheter and associated method disclosed in the '807 patent is that it relies on tissue impedance measurement as the sole manner for determining the position and orientation of the catheter. Furthermore, if the catheter electrodes used in the impedance measurements are also used with an ECG device to collect body surface and intracardiac ECG signals, the impedance measuring components of the '807 patent would require a separate ground relative to the ECG device, which complicates the circuitry.

SUMMARY OF THE INVENTION

The present invention is directed to a novel system and method for detecting electrode-tissue contact. The system of the invention comprises a catheter comprising a body having a proximal end and a distal end, the distal end having a distal tip. The catheter further comprises a contact electrode, preferably positioned at the catheter distal tip, and a location sensor. The system of the invention further comprises a reference electrode and a contact detection circuit. The contact detection circuit comprises a signal generator for sending test signals to the contact electrode and to the reference electrode. The contact detection circuit further comprises a circuit to measure a differential electrical response to the test signals, the differential electrical response being indicative of contact of the contact electrode with tissue.

In the system of the invention, the reference electrode is preferably positioned on the catheter comprising the contact electrode and the location sensor. The reference electrode is further preferably protected from making contact with tissue. In one embodiment, the reference electrode is protected from tissue contact by a membrane covering the electrode. The membrane permits contact of the reference electrode with blood but does not permit contact of the reference electrode with tissue. In another embodiment, the reference electrode is protected from making tissue contact by recessing the electrode relative to the catheter body.

The system of the invention preferably further comprises a return electrode, which functions as a sink for the test signals to the contact electrode and to the reference electrode. In some embodiments, the return electrode is adapted for positioning internal to the body. For example, the return electrode may be positioned on the catheter comprising the contact electrode and the location sensor. In other embodiments, the return electrode is adapted for contact with skin external to the body. The return electrode may be dedicated for measuring differential signals with the contact electrode and the reference electrode. The return electrode is preferably connected to isolated ground, preferably, to an electrocardiogram device isolated ground.

The location sensor contained in the catheter used in the system of the invention may be of any type known in the art, for example, acoustic, magnetic or electromagnetic location sensors. Preferably, the location sensor is an electromagnetic location sensor.

In one embodiment, the system of the invention comprises a catheter comprising a body having a proximal end and a distal end, the distal end having a distal tip. The catheter further comprises a contact electrode positioned at the catheter distal tip, a location sensor and a reference electrode. The system of the invention further comprises a contact detection circuit. The contact detection circuit comprises a signal generator for sending test signals to the distal tip contact electrode and to the reference electrode. The contact detection circuit further comprises a circuit to measure a differential electrical response to the test signals, the differential electrical response being indicative of contact of the distal tip contact electrode with tissue. The system of the invention further comprises a return electrode which functions as a sink for the test signals to the distal tip contact electrode and to the reference electrode. The circuit to measure a differential electrical response to the test signals comprises a first differential amplifier and a second differential amplifier. The first differential amplifier is used to measure a first electrical difference signal between the distal tip electrode and the return electrode. The second differential amplifier is used to measure a second electrical difference signal between the reference electrode and the return electrode. The system of the invention preferably further comprises a third differential amplifier to measure an electrical difference signal between the first electrical difference signal and the second electrical difference signal.

The first differential amplifier preferably measures the voltage difference between the distal tip electrode and the return electrode. The second differential amplifier preferably measures the voltage difference between the reference electrode and the return electrode. The third differential amplifier preferably measures the voltage difference between the first amplifier and the second amplifier. The electrical difference signal measured by the third differential amplifier is preferably rectified by a synchronous detector.

The gains of the first amplifier and the second amplifier are preferably adjusted such that the ratio of the gain of the first amplifier to the gain of the second amplifier is proportional to the ratio of the tip electrode area to the reference electrode area. When so adjusted, the output of the third amplifier will be a null signal when both the tip electrode and the reference electrode are in blood and neither electrode is in contact with tissue.

In this embodiment of the system of the invention, the distal tip electrode is preferably supplied with a first constant current and the reference electrode is supplied with a second constant current, the first current being equal to the second current. The return electrode is preferably driven with a third constant current opposite in phase with the first constant current and the second current.

In another embodiment, the system of the invention for detecting electrode-tissue contact comprises a catheter comprising a body having a proximal end and a distal end, the distal end having a distal tip. The catheter further comprises a contact electrode positioned at the catheter distal tip, a location sensor and a reference electrode. The system of the invention further comprises a contact detection circuit. The contact detection circuit comprises a signal generator for sending test signals to the distal tip contact electrode and to the reference electrode. The contact detection circuit further comprises a circuit to measure a differential electrical response to the test signals, the differential electrical response being indicative of contact of the distal tip contact electrode with tissue. The system further comprises a return electrode which functions as a sink for the test signals to the distal tip contact electrode and to the reference electrode. The circuit to measure a differential electrical response to the test signals comprises a bridge circuit comprising a first resistive element and a second resistive element. The first resistive element and the second resistive element each have a first side and a second side. The first side of the first resistive element is electrically connected with the first side of the second resistive element. The second side of the first resistive element is electrically connected with the reference electrode and the second side of the second resistive element is electrically connected with the distal tip contact electrode. The bridge circuit has a first input between the first resistive element and the second resistive element and a second input electrically connected to the return electrode. The bridge has a first output between the first resistive element and the reference electrode and a second output between the second resistive element and the distal tip contact electrode. The bridge outputs are preferably connected to a differential amplifier which measures a bridge output voltage indicative of contact of the distal tip contact electrode with tissue. The output of the differential amplifier is preferably rectified by a synchronous detector.

In one variation of this embodiment, the first resistive element is a first resistor and the second resistive element is a second resistor. The ratio of the resistance of the first resistor to the resistance of the second resistor is preferably proportional to the ratio of the tip electrode area to the reference electrode area.

In another variation on this embodiment, the first resistive element is a first high output impedance buffer and the second resistive element is a second high output impedance buffer. The ratio of the output currents of the first high output impedance buffer to the second high output impedance buffer is preferably proportional to the ratio of the tip electrode area to the reference electrode area.

Another embodiment of the system of the invention for detecting electrode-tissue contact comprises a catheter comprising a body having a proximal end and a distal end, the distal end having a distal tip. The catheter further comprises a contact electrode positioned at the catheter distal tip, a location sensor and a reference electrode. The system of the invention further comprises a contact detection circuit. The contact detection circuit comprises a signal generator for sending test signals to the distal tip contact electrode and to the reference electrode. The contact detection circuit further comprises a circuit to measure a differential electrical response to the test signals, the differential electrical response being indicative of contact of the distal tip contact electrode with tissue. The system further comprises a return electrode which functions as a sink for the test signals to the distal tip contact electrode and to the reference electrode. The circuit to measure a differential electrical response to the test signals comprises a first current sensor for measuring the current to the reference electrode and a second current sensor for measuring the current to the distal tip electrode. The current sensors are preferably selected from current transformers and Hall effect sensors. The ratio of the gain of the first current sensor to the gain of the second current sensor is preferably proportional to the ratio of the tip electrode area to the reference electrode area. The current sensors preferably have outputs connected to a differential amplifier that measures a voltage indicative of contact of the distal tip electrode with tissue. The differential amplifier preferably has an output rectified by a synchronous detector.

Another aspect of the invention is directed to a method for detecting electrode-tissue contact. The method of the invention comprises providing a catheter comprising a body having a proximal end and a distal end, the distal end having a distal tip. The catheter further comprises a contact electrode adapted for contact with tissue, preferably positioned at the catheter distal tip, and a location sensor. The method of the invention further comprises providing a reference electrode, which is preferably positioned on the catheter comprising the contact electrode and the location sensor. The method of the invention further comprises the steps of providing test signals to the contact electrode and to the reference electrode, and measuring a differential electrical response to the test signals, the differential electrical response being indicative of contact of the contact electrode with tissue.

The location sensor contained in the catheter used in the method of the invention is preferably an electromagnetic sensor.

In practicing the method of the invention, the reference electrode is preferably protected from making contact with tissue. In one embodiment, the reference electrode is protected from making tissue contact by a membrane covering the reference electrode; the membrane permitting contact of the reference electrode with blood but not permitting contact of the reference electrode with tissue. Alternatively, the reference electrode may be protected from making tissue contact by being recessed relative to the catheter body.

In one embodiment, the method of the invention comprises providing a catheter comprising a body having a proximal end and a distal end, the distal end having a distal tip. The catheter further comprises a contact electrode adapted for contact with tissue positioned at the catheter distal tip, a location sensor and a reference electrode. The method of the invention further comprises the steps of providing test signals to the distal tip contact electrode and to the reference electrode, and measuring a differential electrical response to the test signals, the differential electrical response being indicative of contact of the contact electrode with tissue. The measurement of the differential electrical response to the test signals comprises the steps of measuring a first electrical difference signal between the distal tip contact electrode and a return electrode; measuring a second electrical difference signal between the reference electrode and the return electrode; and comparing the first electrical difference signal with the second electrical difference signal to detect contact of the distal tip contact electrode with tissue.

In this embodiment of the method of the invention, the signals provided to the distal tip and reference electrodes are preferably constant current signals.

The comparison of the first and second electrical difference signals preferably comprises feeding the signals to a differential amplifier to produce a third electrical difference signal indicative of electrode-tissue contact. The first and second electrical difference signals are preferably adjusted to provide a null difference signal from the differential amplifier when the distal tip electrode and the reference electrode are both in blood and neither electrode is in contact with tissue.

In another embodiment, the method of the invention for detecting electrode-tissue contact comprises providing a catheter comprising a body having a proximal end and a distal end, the distal end having a distal tip. The catheter further comprises a contact electrode adapted for contact with tissue positioned at the catheter distal tip, a location sensor and a reference electrode. The method of the invention further comprises the steps of providing test signals to the distal tip contact electrode and to the reference electrode, and measuring a differential electrical response to the test signals, the differential electrical response being indicative of contact of the contact electrode with tissue. The measurement of the differential electrical response to the test signals comprises the steps of providing a bridge circuit comprising a first resistive element and a second resistive element. The first resistive element and the second resistive element each have a first side and a second side. The first side of the first resistive element is electrically connected to the first side of the second resistive element. The second side of the first resistive element is electrically connected with the reference electrode and the second side of the second resistive element is electrically connected with the distal tip electrode. The bridge circuit has a first input between the first resistive element and the second resistive element and a second input electrically connected to a return electrode. The bridge circuit further has a first output between the first resistive element and the reference electrode and a second output between the second resistive element and the distal tip electrode. The method of the invention further comprises measuring a signal across the bridge outputs to detect contact of the distal tip electrode with tissue. The signal across the bridge outputs is preferably measured with a differential amplifier, and is preferably adjusted to provide a null signal when the distal tip electrode and the reference electrode are both in blood and neither electrode is in contact with tissue.

In one variant of this embodiment of the method of the invention, the first resistive element comprises a first resistor and the second resistive element comprises a second resistor. In another variant, the first resistive element comprises a first high output impedance buffer and the second resistive element comprises a second high output impedance buffer.

In another embodiment, the method of the invention for detecting electrode-tissue contact comprises providing a catheter comprising a body having a proximal end and a distal end, the distal end having a distal tip. The catheter further comprises a contact electrode adapted for contact with tissue positioned at the catheter distal tip, a location sensor and a reference electrode. The method of the invention further comprises the steps of providing test signals to the distal tip contact electrode and to the reference electrode, and measuring a differential electrical response to the test signals, the differential electrical response being indicative of contact of the contact electrode with tissue. The measurement of the differential electrical response to the test signals comprises the steps of measuring current to the reference electrode with a first current sensor and measuring current to the distal tip electrode with a second current sensor. The outputs of the first current sensor and the second current sensor are connected to a differential amplifier to measure a differential voltage indicative of contact of the distal tip contact electrode with tissue. The current sensors are preferably of the current transformer or Hall effect type. The current sensors preferably have outputs connected to a differential amplifier that measures a voltage indicative of contact of the distal tip electrode with tissue. The signals from the current sensors are preferably adjusted to provide a null signal from the differential amplifier when the distal tip electrode and the reference electrode are both in blood and neither electrode is in contact with tissue.

In another embodiment, the method of the invention for detecting electrode-tissue contact comprises providing a catheter comprising a body having a proximal end and a distal end, the distal end having a distal tip. The catheter further comprises a contact electrode adapted for contact with tissue positioned at the catheter distal tip, a location sensor and a reference electrode. The method of the invention further comprises the steps of providing test signals to the distal tip contact electrode and to the reference electrode, and measuring a differential electrical response to the test signals, the differential electrical response being indicative of contact of the contact electrode with tissue. The measurement of the differential electrical response to the test signals comprises the steps of measuring a first impedance between the distal tip electrode and a return electrode and a measuring a second impedance between the reference electrode and a return electrode. The first and second impedances are compared to detect contact of the catheter distal tip contact electrode with tissue.

The method of the invention optionally further comprises collecting electrical information from the contact electrode, preferably positioned at the catheter distal tip, and location information from the location sensor at a plurality of points on the tissue. An electrical map of the tissue is then generated from the electrical and location information. The electrical and location information at each point in the map is weighted in accordance with contact being detected between the contact electrode and the tissue at each point.

The method of the invention optionally further comprises collecting electrical information from the contact electrode, preferably positioned at the catheter distal tip, and mechanical information from the location sensor, respectively at a plurality of points on the tissue. An electromechanical map of the tissue is then generated from the electrical and mechanical information. The electrical and mechanical information at each point in the map is weighted in accordance with contact being detected between the contact electrode and the tissue at each point.

The method of the invention optionally further comprises delivering ablation energy to the contact electrode, preferably positioned at the catheter distal tip, in accordance with the electrode being in contact with tissue.

It is an object of the invention to provide a system and method for detecting contact of an electrode with tissue.

It is another object of the invention to provide a differential system and method for detecting electrode-tissue contact with a contact electrode in comparison with a reference electrode.

It is another object of the invention to provide a differential system and method for detecting electrode-tissue contact with a contact electrode in comparison with a reference electrode not in contact with tissue.

It is another object of the invention to provide a system and method for detecting electrode-tissue contact in a system comprising a highly accurate location sensor.

It is another object of the invention to provide a system and method for detecting electrode-tissue contact for use in cardiac mapping procedures.

It is another object of the invention to provide a system and method for detecting electrode-tissue contact for use in cardiac ablation procedures.

These and other objects, features and advantages of the present invention will be more readily apparent from the detailed description set forth below, taken in conjunction with the accompanying drawings.

DETAILED DESCRIPTION OF THE PREFERRED EMBODIMENTS

The present invention is directed to a novel system as well as a novel method for detecting contact of an electrode with tissue such as the wall of a chamber of a heart. The present invention is particularly suitable for use with systems and methods for mapping the electrical characteristics of a chamber of a heart, or for performing electro-therapeutic procedures such as cardiac ablation.

The method and system of the invention for detecting electrode-tissue contact are based on differential impedance measurements. Impedance values of tissue such as the cardiac wall tend to be larger than the impedance of blood. The method and system of the invention measure the impedance between a catheter contact electrode, preferably positioned on the catheter distal tip, and a return electrode. The method and system of the invention also simultaneously measures the impedance between a reference electrode and a return electrode. The reference electrode is internal to the body and is preferably prevented from making contact with tissue. By simultaneously measuring and comparing the impedance across the contact electrode and return electrode relative to the impedance across a reference electrode to a return electrode, the method and system of the present invention overcomes the above-enumerated limitations of many of the prior art contact detection methods.

As used herein, the term "tissue" is meant to describe all solid or semi-solid cellular matter in the body, such as muscle, nerve, connective tissue, vasculature and bone. Blood and other liquid matter, such as lymph, interstitial fluids or other fluids in the body, are excluded from the definition of "tissue" as defined herein.

Figure 1:
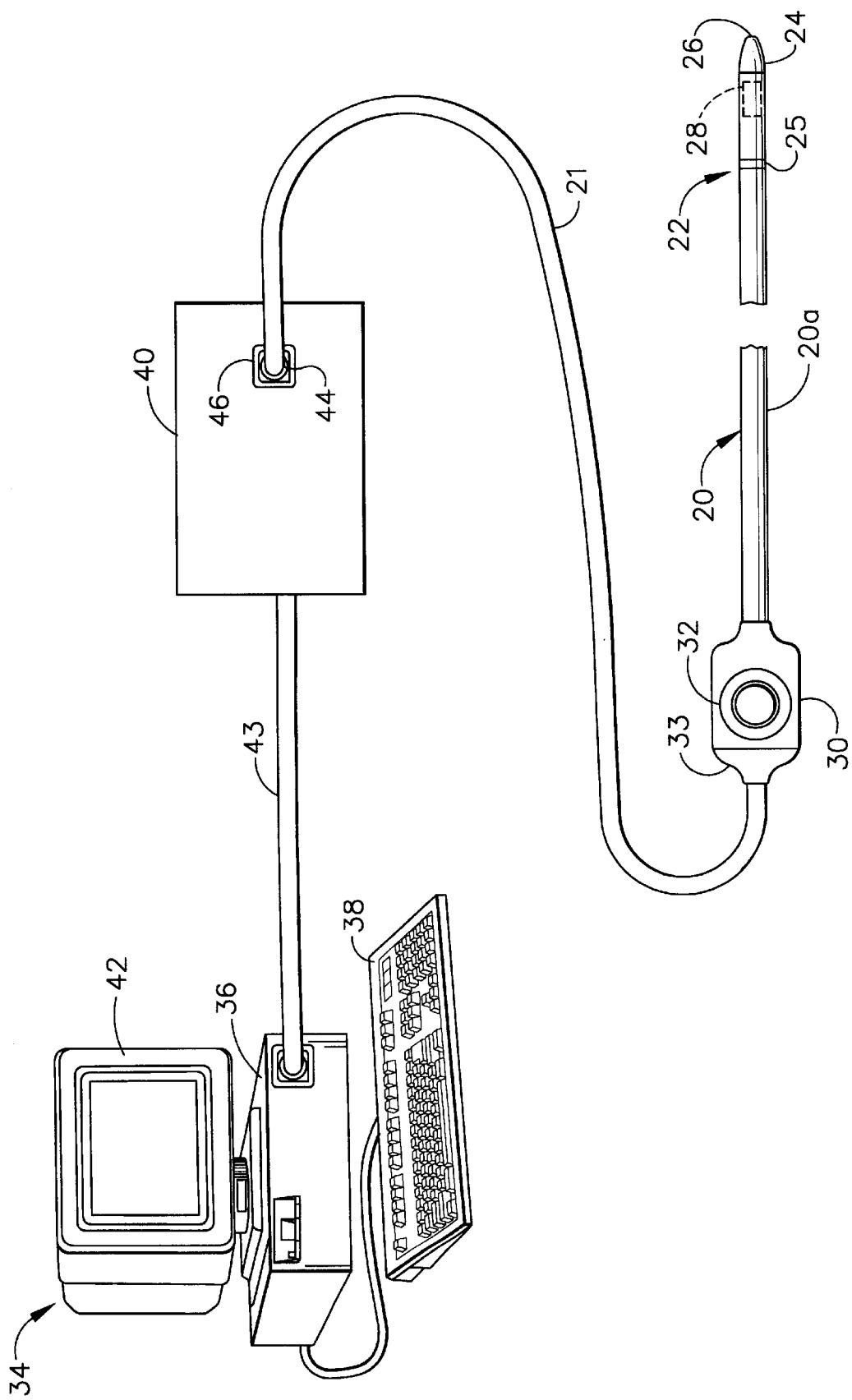
FIG. 1 is a schematic illustration showing elements of a cardiac diagnostic and therapeutic system incorporating the system and method of the invention.
Figure 2:
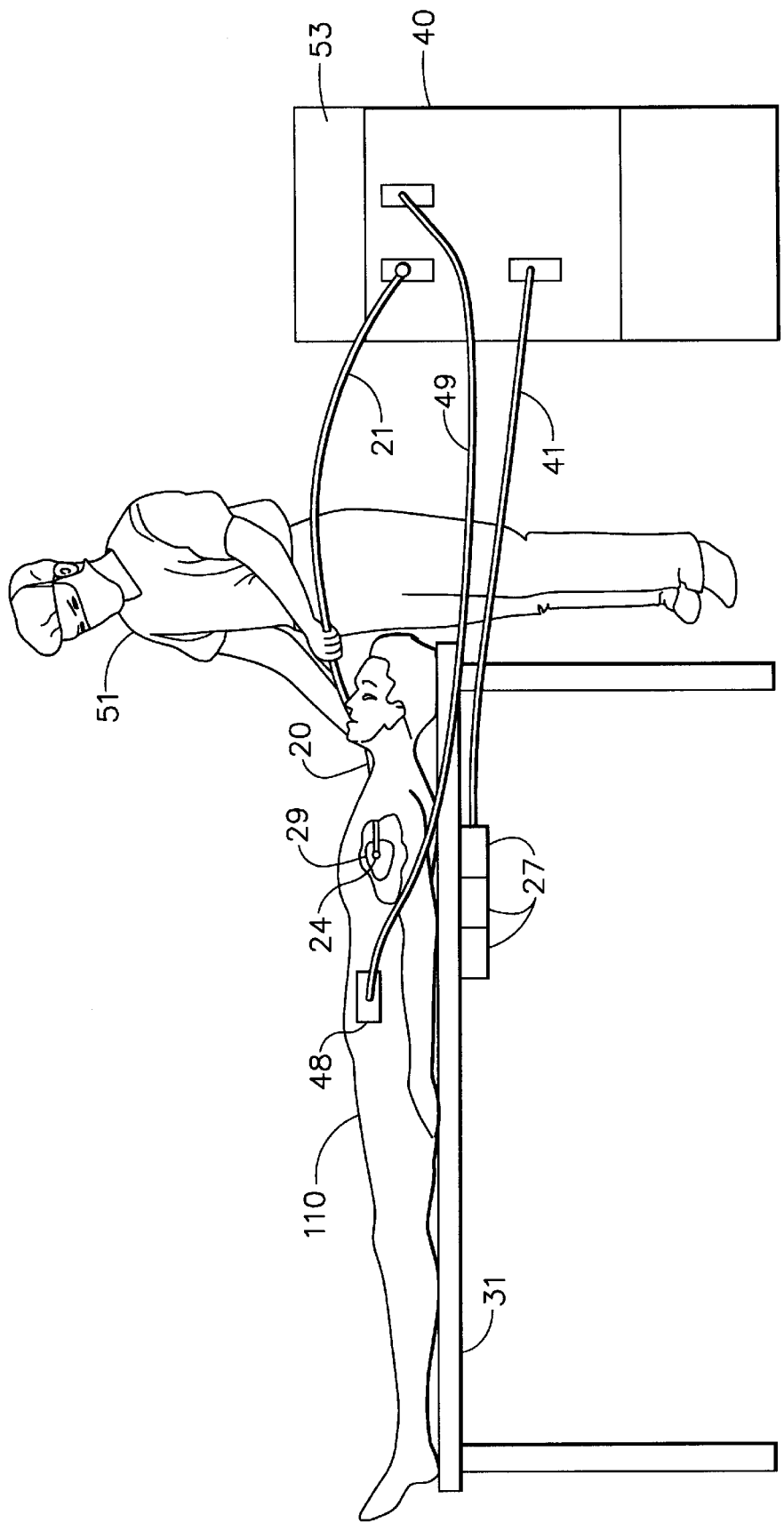
FIG. 2 is a schematic illustration showing additional components used in the system of FIG. 1 in use on a patient.

One embodiment of the present invention, included within a diagnostic mapping and therapeutic delivery system, generally designated 18, is best shown in FIG. 1. The system comprises a catheter 20 for insertion into the human body, and preferably, into a chamber of a human heart 29 (FIG. 2). The catheter 20 includes a catheter body 20a having a distal end 22. The distal end 22 includes a contact electrode 24 at distal tip 26 for measuring the electrical properties of the heart tissue. Contact electrode 24 is also useful for sending electrical signals to the heart for diagnostic purposes, e.g., for pace mapping, and/or for therapeutic purposes, e.g., for ablating defective cardiac tissue. While contact electrode 24 is designed to be in contact with tissue when performing its functions of receiving electrical signals from and transmitting electrical signals to the heart, it should be understood that contact electrode 24 is not always in contact with tissue. For example, contact electrode 24 may not be in contact with tissue as it is being advanced through the vasculature to the heart, or when it is being directed from one point to another point within the heart chamber. Accordingly, it is an object of the system and method of the invention to detect contact of the contact electrode with tissue.

Distal end 22 of catheter 20 further includes reference electrode 25 for providing an internal reference measurement of impedance while the reference electrode 25 is in contact with blood but is not in contact with tissue. Distal end 22 of catheter 20 further includes a location sensor 28 that generates signals used to determine the position and orientation of the catheter within the body. Location sensor 28 is preferably adjacent to distal tip 26 of catheter 20. There is preferably a fixed positional and orientational relationship of location sensor 28, tip 26 and electrode 24.

Catheter 20 preferably includes a handle 30, which includes controls 32 to steer the distal end 22 of the catheter 20 in a desired direction, such as deflecting the distal end 22, or to position and/or orient it as desired.

The system 18, as shown in FIGS. 1 and 2, further comprises a console 34, which enables the user to observe and regulate the functions of catheter 20. Console preferably includes a computer 36, keyboard 38, and display 42. Computer 36 contains control circuits to permit control and operation of the system and to start and stop the collection of data from the catheter's tip electrode 24, reference electrode 25 and from location sensor 28. Computer 36 further uses the electrical and or mechanical and location information acquired by catheter electrodes 24 and 25 and location sensor 28 and processed by signal processing circuits 40 in reconstruction and visualization of an electrical or electromechanical map of a chamber of the heart.

Signal processing circuits 40 typically receive, amplify, filter and digitize signals from catheter 20, including signals generated by location sensor 28, tip electrode 24 and reference electrode 25. Circuits 40 further compute the position and orientation of the catheter as well as the electrical characteristics of the heart chamber from the signals generated by location sensor 28 and tip electrode 24. Circuits 40 also process body surface electrocardiogram signals. The digitized signals generated by signal processing circuits 40 are received and used by computer 36 to reconstruct and visualize an electrical or electromechanical map of the heart chamber. Circuits 40 also contain contact detection circuitry, including a signal generator 56 (FIG. 3) which sends test signals to tip electrode 24, reference electrode 25 and return electrode 48, as well as circuitry to measure the differential electrical response to these test signals. Return electrode 48 is coupled to circuits 40 via cable 49 wherein return electrode 48 functions as a sink for the test signals.

When applied external to the patient's body 110 as shown in FIG. 2, return electrode 48 is preferably relatively large to provide low impedance between the return electrode 48 and the body 110. For example, Electrosurgical Patient Plate model 1149F, supplied by 3M of St. Paul, Minn., which has an area of approximately 130 $cm^2$, may be satisfactorily used as the return electrode in the system and method of the invention.

Alternatively, appropriate circuitry may be associated with the catheter 20 itself so that circuits 40 receive signals that are already amplified, filtered and/or digitized.

Catheter 20 is coupled to circuits 40 via an extension cable 21, which at its proximal end comprises a connector 44 adapted to fit in a mating receptacle 46 on circuits 40. The distal end of cable 21 comprises a receptacle 33 which connects to catheter handle 30. Receptacle 33 is preferably configured to receive catheters of a specific model, and preferably includes user-evident identification of the specific model. One of the advantages in using cable 21 is the ability to connect different models and types of catheters, such as those catheters having different handle configurations, to the same circuits 40. Different cables 21 can be used to connect a large variety of catheters to circuits 40. Another advantage in having a separate cable 21 is in the fact that the cable 21 does not come into contact with patients and therefore it is possible to re-use the cable 21 without sterilization.

Circuits 40 contain an isolation barrier to electrically isolate all parts of the system in contact with the patient from console 34. Data transfer from circuits 40 to computer 36 is effected using such devices as insulating transformers, optocouplers and the like.

Additional components used in system 18 with catheter 20 of the present invention are illustrated schematically in FIG. 2. A physician 51 inserts catheter 20 through an incision in the vasculature, e.g., using an intravascular approach, into a chamber of a heart 29 of a patient 110, so that distal tip electrode 24 and location sensor 28 are inside the chamber. In accordance with an exemplary location sensor described in PCT patent application number WO 96/05768, filed Jan. 24, 1995, and U.S. Pat. No. 5,391,199, which are assigned to the assignee of the present application and whose disclosures are incorporated herein in their entirety by reference, sensor 28 generates signals in response to externally applied magnetic fields generated by electromagnetic field generator coils 27 fixed to operating table 31 in proximity to patient 110. The magnitude of the signals generated by sensor 28 depends on the position and orientation of the sensor in the applied magnetic field. Field generator coils 27 are connected via cable 41 to driver circuits which are part of signal processing circuits 40. Circuits 40 are connected to computer 36 (FIG. 1) via cable 43. Computer 36 controls the operation of the generator coils 27 and the overall system 18.

Alternatively, the system of the invention may employ field generator coils in the catheter and sensors external to the patient.

While the catheter used in the system and method of the invention has been described herein as containing a single contact electrode at its distal tip and a single reference electrode, the system and method of the invention may employ catheters of different designs. For example, the tip electrode may be of a unipolar or a bipolar design. In the bipolar configuration, the catheter would have another ring electrode proximal to the tip electrode. Alternatively, the catheter may have a plurality of ring electrodes along its length.

While the system and method of the invention are described herein with reference to electromagnetic sensors, any other location sensor that provides three-dimensional position information and, optionally, orientation information, may be used in the practice of the invention. Illustrative sensors that are also useful include acoustic sensors and magnetic sensors. For example, acoustic sensors of the type disclosed in U.S. Pat. No. 5,409,000 and in PCT application WO 99/05971, the disclosures of which are incorporated herein in their entirety by reference, may be used in accordance with the system and method of the invention.

As disclosed in U.S. Pat. No. 5,391,199, mapping the electrical activity of the heart is performed by positioning the distal tip 26 of catheter 20 at a site within the heart, sensing location and electrical information at the site, processing the sensed location and electrical information at the site to create a data point, and repeating these steps a sufficient number of times to create a map of the heart's electrical pathways. For an accurate map of the chamber electrical activity, location and electrical data are preferably sensed when the tip electrode 24 is in contact with the cardiac wall at each site.

Having identified a lesion responsible for an aberrant electrical pathway from the resultant electrical map of the heart chamber, the aberrant pathway may be treated by ablating the intracardiac surface at the lesion site. As shown in FIG. 2, ablation is typically performed by supplying RF energy to the site from ablation power source 53 via circuits 40 and cable 21 to tip electrode 24 at distal end 22 of catheter 20. Ablation is most effectively performed when tip electrode 24 is in contact with the cardiac wall. Absence of contact or poor contact of tip electrode 24 with the heart wall leads to dissipation of the RF energy in the blood, as well as possible fouling of the tip electrode. Accordingly, it is important that both mapping and ablation be accompanied by methods and systems for detecting electrode-tissue contact.

Figure 3:
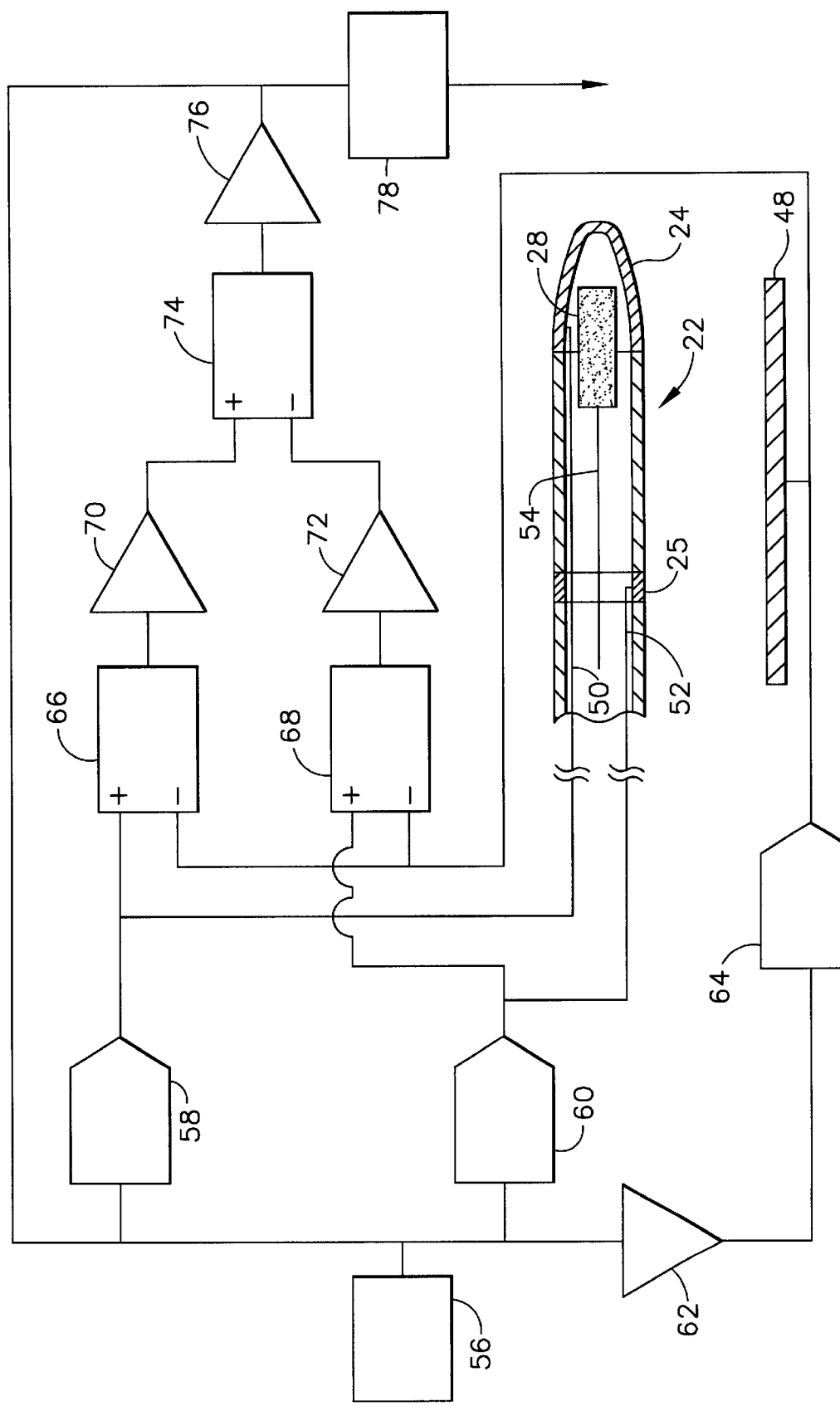
FIG. 3 is a schematic diagram showing one embodiment of a circuit used for detecting electrode-tissue contact.

One embodiment of a circuit for detecting electrode-tissue contact in conjunction with the system of FIG. 1 is shown in FIG. 3. Distal end 22 of catheter 20 is shown in longitudinal cross-section. Tip electrode 24, reference electrode 25 and location sensor 28 are connected by wires 50, 52 and 54, respectively, to catheter handle 30 from which electrical connections are made to signal processing circuits 40. Signal generator 56, contained within circuits 40, sends a high frequency alternating current (AC) signal, preferably in the frequency range of about 10 kHz to about 100 kHz, to distal tip contact electrode 24 and to reference electrode 25 via high output impedance buffers 58 and 60, respectively. A signal frequency of about 50 kHz is most preferred. The current to distal tip electrode 24 is equal to the current to reference electrode 25. Return electrode 48 is also driven by signal generator 56. The signal to return electrode 48 is first inverted in phase by inverter 62 and conditioned by high output impedance buffer 64. The current of the signals driving tip electrode 24, reference electrode 25 and return electrode 48 should be below the level that would stimulate cardiac tissue. At 50 kHz, generally accepted safety standards dictate that the current should not exceed 0.5 milliamps (See for example CEI IEC 601-1, Medical Electrical Equipment Part 1 - General Requirements for Safety, Bureau Central de la Commission Electrotechnique Internationale, Geneva Switzerland, 1988). First differential amplifier 66 measures a difference signal, specifically, the voltage across distal tip electrode 24 and return electrode 48. A second differential amplifier 68 is used to measure the voltage across reference electrode 25 and return electrode 48. Signals from differential amplifiers 66 and 68 are further amplified by amplifiers 70 and 72, respectively. The outputs of amplifiers 70 and 72 are, in turn, fed to differential amplifier 74. The differential output signal from differential amplifier 74 is further amplified by amplifier 76. The amplified signal from amplifier 76 is then sent to synchronous detector 78, which transforms the AC signal to a direct current (DC) signal and also decreases the sensitivity of the system to external noise. The signal from the synchronous detector 78 is then used by signal processing circuits 40.

When the tip and reference electrodes are both in a common medium, i.e., in the blood, and neither electrode is in contact with tissue, the voltages measured at the tip and reference electrodes against the common return electrode will be inversely proportional to the area of the respective electrodes. Accordingly, the ratio of the gains of amplifiers 70 and 72 are preferably adjusted so as to be proportional to the ratio of the areas of tip electrode 24 and reference electrode 25. Under these conditions, i.e., when distal tip electrode 24 and reference electrode 25 are both in blood and not in contact with tissue and when the amplifier gains are adjusted as described above, the signals leaving amplifiers 70 and 72 will be of equal voltage and the output of differential amplifier 74 and amplifier 76 will be a null signal of zero volts. When tip electrode 24 is brought into contact with tissue such as the cardiac wall, which has a higher impedance than blood, and when reference electrode 25 remains in the blood and does not contact the tissue, the voltage across tip electrode 24 and return electrode 48 will exceed the voltage across reference electrode 25 and return electrode 48, resulting in a non-zero voltage signal from differential amplifier 74 and amplifier 76. This non-zero signal, which detects the change in the impedance across catheter tip electrode 24 and return electrode 48 when tip electrode 24 contacts tissue, is used by the system electronics of signal processing circuits 40 to provide an audible or visible signal indicative of tissue contact.

Tissue contact is signaled by a variety of techniques. One form of signaling of tissue contact, for example, is the illumination of a light or LED on an instrument panel. Alternatively, tissue contact may be signaled by a meter, displayed on a computer monitor for example, along with other system parameters.

Figure 13A:
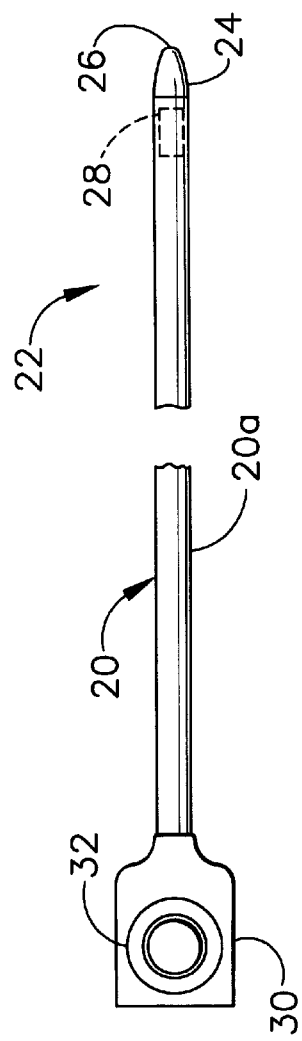
FIG. 13A is a schematic drawing of a catheter of an alternate design for use in the system and method of the invention.
Figure 13B:
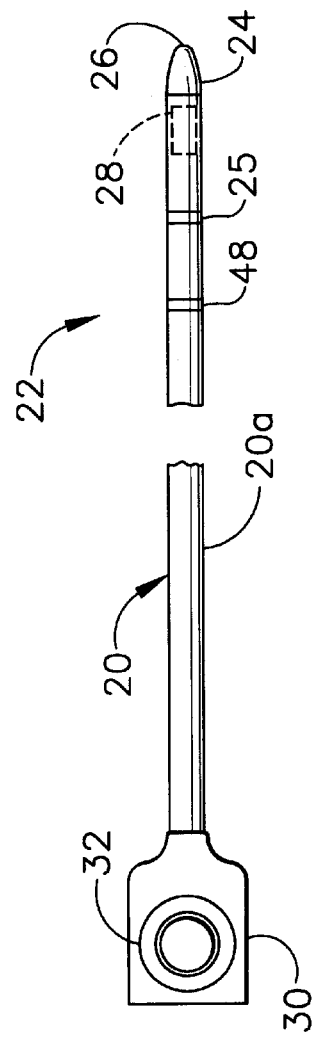
FIG. 13B is a schematic drawing of a catheter of another design for use in the system and method of the invention.

A number of variations are envisioned for the present embodiment of the system of the invention. For example, in the embodiment described above, reference electrode 25 is positioned on mapping/ablation catheter 22 comprising distal tip electrode 24 and location sensor 28. Alternatively, reference electrode 25 may be positioned on a separate catheter contained in the vasculature. FIG. 13A shows a schematic view of a catheter 20 of an alternate design for use in the system and method of the invention. Catheter 20 of FIG. 13A does not contain a reference electrode. In use in the system and method of the invention, a reference electrode would be provided with a second catheter (not shown). Likewise, return electrode 48 may be incorporated on the catheter 20 containing the distal tip electrode 24 and location sensor 28, in which case return electrode 48 would be present in the body during use. FIG. 13B shows a schematic view of a catheter 20 of an alternate design which incorporates both a reference electrode 25 and a return electrode 48.

Alternatively, catheter 20 may be equipped with a thermocouple at distal tip electrode 24 for monitoring of the electrode temperature during ablation and for control of ablation energy delivery to the electrode during ablation.

The system shown in FIG. 3 shows the return electrode 48 driven by signal generator 56. Alternatively, return electrode 48 may be connected to an isolated ground, for example, of an electrocardiogram (ECG) device. The right leg ECG electrode is typically connected in many ECG devices to isolated ground, and would function satisfactorily as a return electrode in the system and method of the invention.

Figure 4:
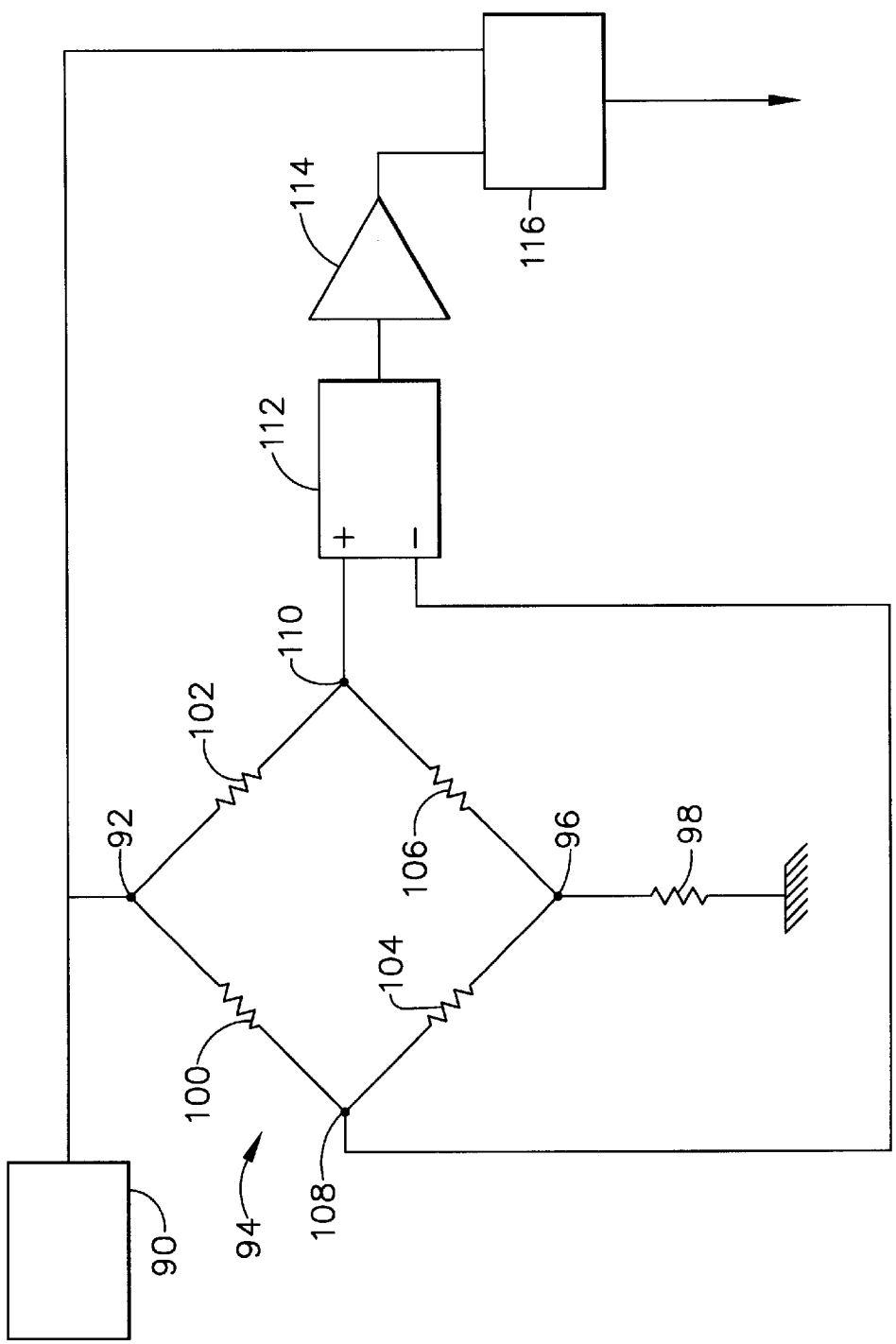
FIG. 4 is a schematic diagram showing a bridge circuit used for detecting electrode-tissue contact.
Figure 5:
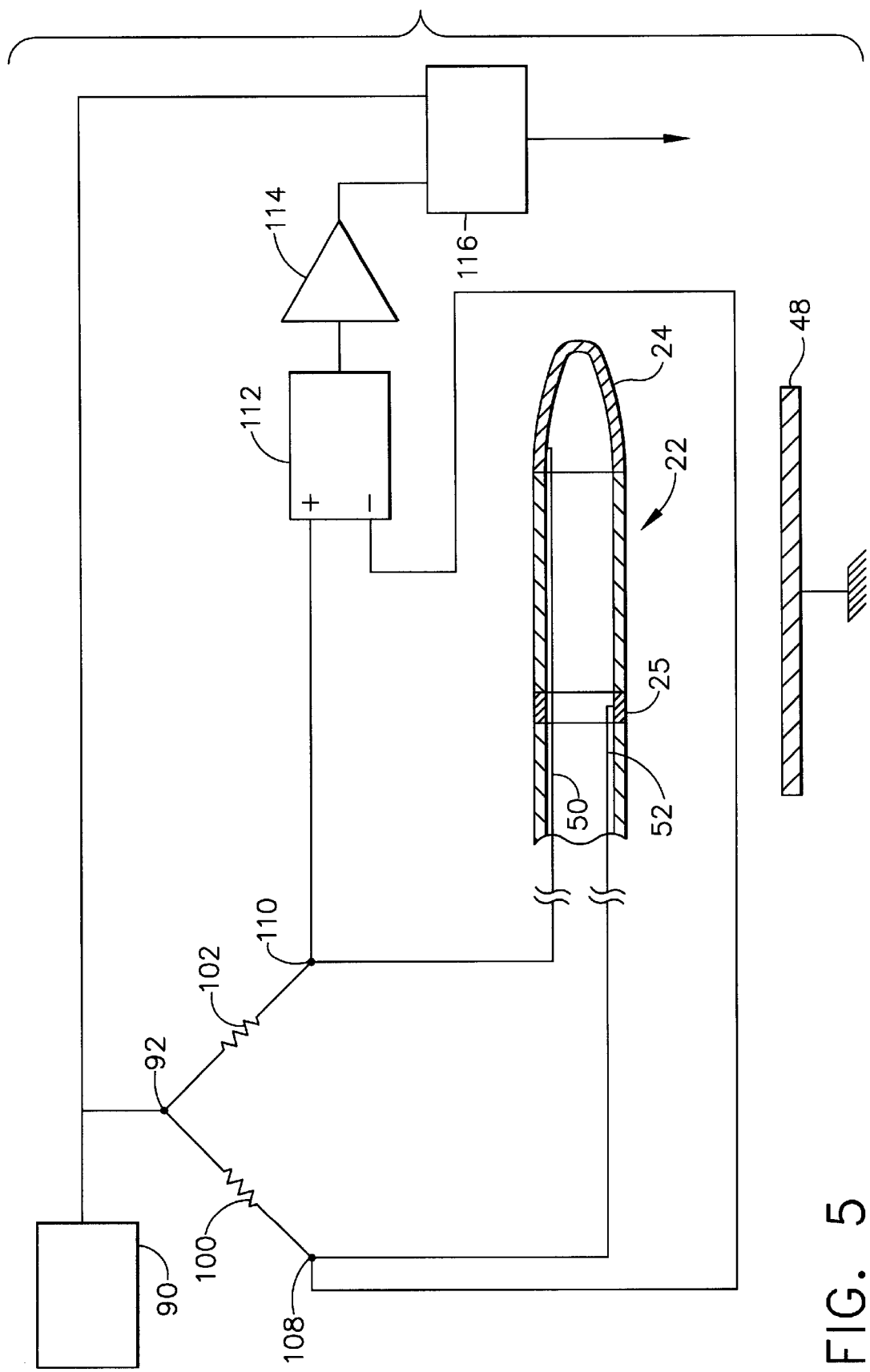
FIG. 5 is a schematic diagram showing one embodiment of the bridge circuit of FIG. 4.
Figure 6:
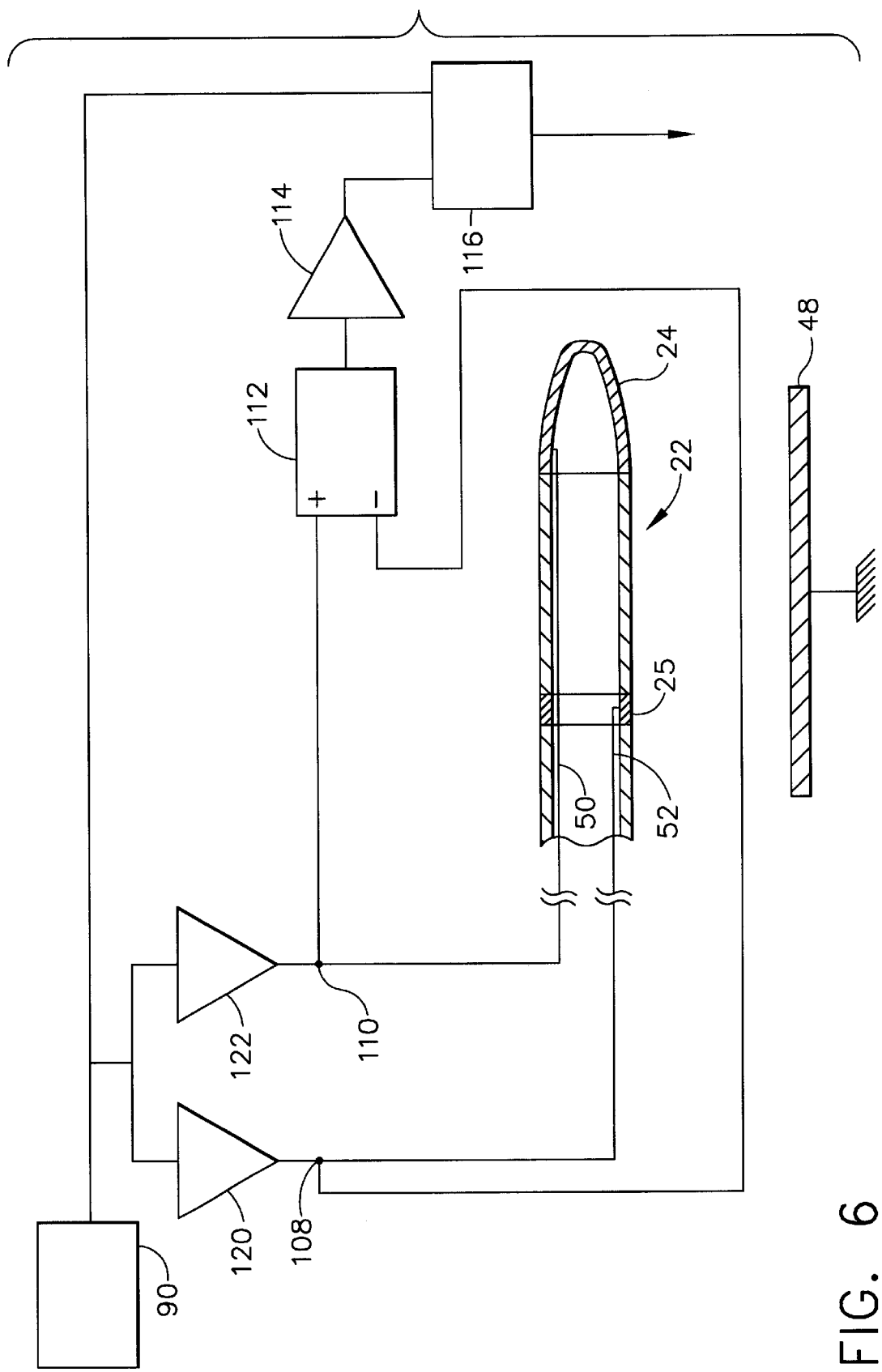
FIG. 6 is a schematic diagram showing another embodiment of the bridge circuit of FIG. 4.

Additional embodiments of circuits for detecting electrode-tissue contact are illustrated in FIG. 5 and FIG. 6. The circuits of these embodiments may be best understood by first considering the circuit shown in FIG. 4, in which signal generator 90 is connected to first input 92 of bridge circuit 94. Second input 96 of bridge circuit 94 is connected to isolated ground via resistor 98. Bridge 94 is composed of a first resistor (R1) 100, a second resistor (R2) 102, a third resistor (R3) 104 and a fourth resistor (R4) 106. First bridge output 108 and second bridge output 110 are connected to differential amplifier 112 for measurement of the output voltage of the circuit. The signal from differential amplifier 112 is further amplified in amplifier 114, from which it is passed to synchronous detector 116.

It is well known that for the bridge circuit of FIG. 4, the output voltage of the bridge across output points 108 and 110 is equal to zero when the following relationship is fulfilled:

$$\frac{R1}{R2} = \frac{R3}{R4}$$

FIG. 5 illustrates one embodiment of a bridge circuit used to detect electrode-tissue contact in the method and system of the invention. The system uses the same catheter as described with reference to FIG. 3. In the embodiment shown in FIG. 5, third resistor R3 (104 of FIG. 4) has been replaced by the signal path from reference electrode 25 to return electrode 48, and fourth resistor R4 (106 of FIG. 4) has been replaced by the signal path from distal tip contact electrode 24 to return electrode 48. Resistor 98 in FIG. 4 is replaced by the signal path from the skin to external return electrode 48. Return electrode 48 is preferably connected to isolated ground, as, for example, to an ECG device isolated ground. For purposes of clarity, location sensor 28 is not shown in the catheters of FIGS. 5, 6 and 7.

If both the tip electrode 24 and reference electrode 25 are in the blood and if both electrodes have the same area, then the impedance from tip electrode 24 to return electrode 48 will equal the impedance from reference electrode 25 to return electrode 48. Under these conditions and if the resistance of resistor R1 100 is equal to the resistance of resistor R2 102, the bridge will have a null output voltage. Contact of tip electrode 24 with tissue having higher impedance than blood will cause the impedance from tip electrode 24 to return electrode 48 to increase over the impedance from reference electrode 25 to return electrode 48, resulting in a non-zero voltage signal from differential amplifier 112 amplifier 114 and synchronous detector 116.

In the event that resistors R1 and R2 have equal resistance and distal tip electrode 24 and reference electrode 25 have unequal surface areas, the impedance along the individual legs of the circuit will be inversely proportional to the area of the respective electrodes. In this condition, the bridge will not have a null output voltage when both tip electrode 24 and reference electrode 25 are in blood and neither electrode is in contact with tissue. Preferably, the resistance of resistors 100 and 102 is adjusted so as to produce a null signal from differential amplifier 112 when distal tip electrode 24 and reference electrode 25 are both in blood and neither electrode is in contact with tissue. This adjustment is achieved when the ratio of resistances of resistor 100 to resistor 102 is proportional to the ratio of the area of tip electrode 24 to the area of reference electrode 25.

For greater sensitivity of the contact detection method, it is preferable that the impedance of resistors 100 and 102 be at least equal to or greater than the impedance from reference electrode 25 to return electrode 48 and from the distal tip electrode 24 to reference electrode 48. Preferably, the impedance of resistors 100 and 102 should be at least about ten times, and, more preferably, at least about 100 times the impedance across reference electrode 25 to return electrode 48 and across tip electrode 24 to return electrode 48.

FIG. 6 shows another embodiment of a bridge circuit used to detect tissue contact in the system and method of the invention. In this embodiment, resistors 100 and 102 of FIG. 5 are replaced by high output impedance buffers 120 and 122. Buffers 120 and 122 convert the constant voltage signal from signal generator 90 to a constant current signal. As with the circuit shown in FIG. 5, if both the tip electrode 24 and the reference electrode 25 are in the blood and if both electrodes have the same surface area, then the tip electrode 24 to return electrode 48 impedance will equal the reference electrode 25 to return electrode 48 impedance. Under these conditions and if the output current of buffer 120 is equal to the output current of buffer 122, the bridge will have a null output voltage. Contact of tip electrode 24 with tissue having higher impedance than blood will cause the tip electrode 24 to return electrode 48 impedance to increase over the reference electrode 25 to return electrode 48 impedance, resulting in a non-zero voltage signal from differential amplifier 112 amplifier 114 and synchronous detector 116.

As with the circuit of FIG. 5, in the event that distal tip electrode 24 and reference electrode 25 have unequal surface areas, the tip electrode 24 to return electrode 48 impedance and reference electrode 25 to return electrode 48 impedance will be inversely proportional to the area of the respective electrodes when tip electrode 24 and reference electrode 25 are both in a common medium. The output currents of high output impedance buffers 120 and 122 are a function of the conversion functions of the individual buffers. Preferably, the conversion functions of buffers 120 and 122 are adjusted so as to produce a null signal from differential amplifier 112 when the distal tip electrode 24 and the reference electrode 25 are both in blood and neither electrode is in contact with tissue. This adjustment is achieved when the ratio of the output current from buffer 120 to the output current from buffer 122 is proportional to the ratio of the area of tip electrode 24 to the area of reference electrode 25.

In order to provide constant current to the tip electrode 24 and reference electrode 25 and in order for this current to be unaffected by electrode-tissue contact, the impedance of buffers 120 and 122 is preferably at least about one thousand times the body impedances displayed across tip electrode 24 to return electrode 48 and across reference electrode 25 to return electrode 48.

Figure 7:
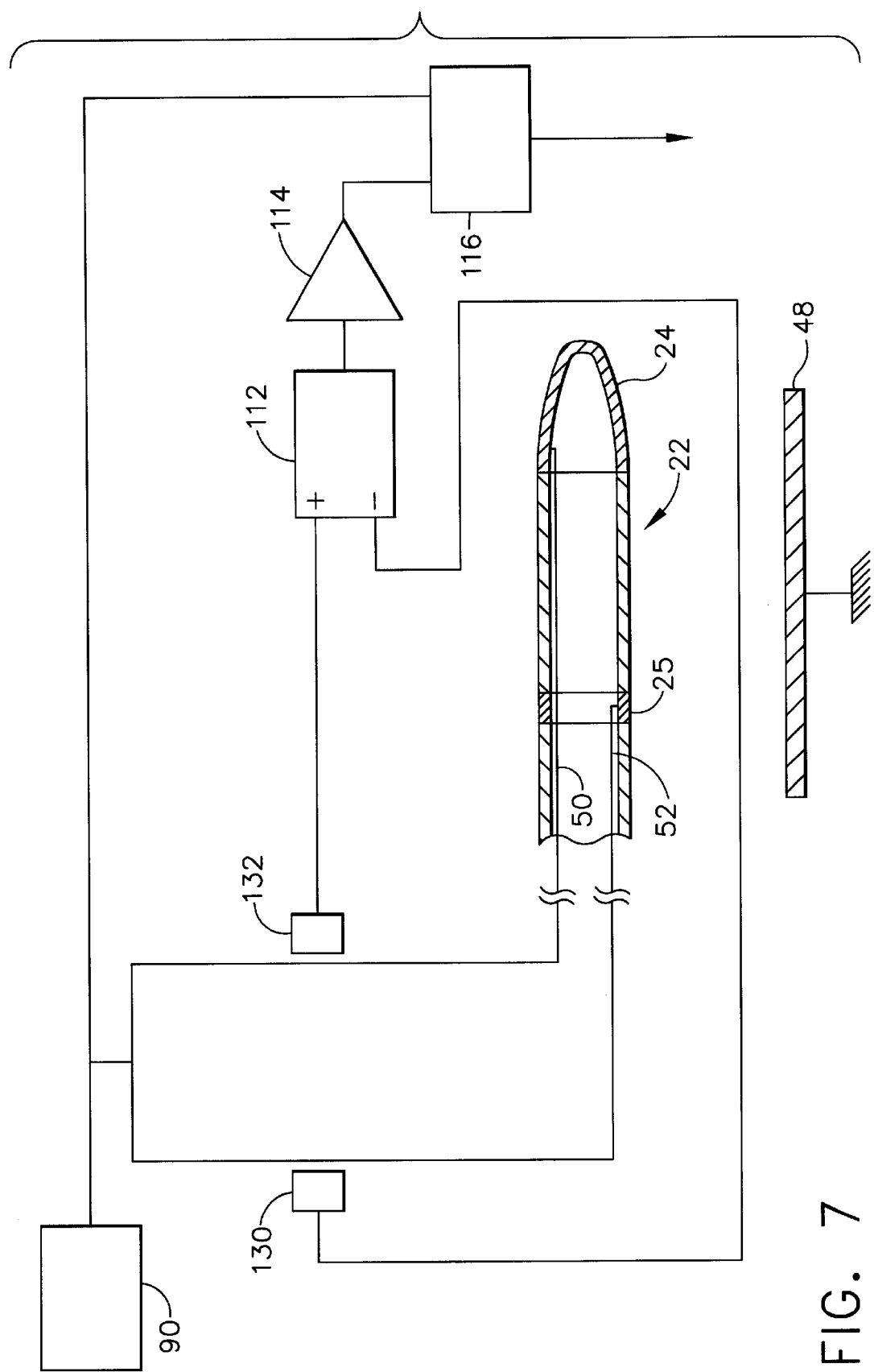
FIG. 7 is a schematic diagram showing another circuit for detecting electrode-tissue contact.

FIG. 7 depicts yet another embodiment of a circuit for detecting electrode-tissue contact. In the embodiment shown in FIG. 7, a high frequency signal is supplied directly to catheter distal tip contact electrode 24 and to reference electrode 25. Current sensors 130 and 132 monitor the current to reference electrode 25 and to tip electrode 24, respectively. Current sensors may be of any type known in the art. For example, current transformers and Hall effect sensors may be used in the practice of the system and method of the invention. Output voltage signals of current sensors 130 and 132 are fed to differential amplifier 112 to measure the relative currents to reference electrode 25 and to tip electrode 24. The output signal from differential amplifier 112 is further amplified by amplifier 114 and transmitted to synchronous detector 116.

As with the previously described embodiments, if tip electrode 24 and reference electrode 25 are both in blood, if neither electrode is in contact with tissue and if both electrodes have the same surface area, then the tip electrode 24 to return electrode 48 impedance will equal the reference electrode 25 to return electrode 48 impedance. Under these conditions the current measured by current sensor 130 will equal the current measured by current sensor 132, and differential amplifier 112 will produce a null voltage. Contact of tip electrode 24 with tissue having higher impedance than blood will cause the tip electrode 24 to return electrode 48 impedance to increase over the reference electrode 25 to return electrode 48 impedance, which will, in turn, result in lower current to distal tip electrode 24 relative to reference electrode 25. Reduction in the current to tip electrode 24 relative to reference electrode 25 will result in a non-zero voltage signal from differential amplifier 112 amplifier 114 and synchronous detector 116.

As in the previously described embodiments, in the event that distal tip electrode 24 and reference electrode 25 have unequal surface areas, the tip electrode 24 to return electrode 48 impedance and the reference electrode 25 to return electrode 48 impedance, and hence the output voltages of current sensors 130 and 132, will be inversely proportional to the area of the respective electrodes when tip electrode 24 and reference electrode 25 are both in a common medium and neither electrode is in contact with tissue. Preferably, the output voltages of sensors 130 and 132 are adjusted so as to produce a null signal from differential amplifier 112 when both the distal tip electrode 24 and the reference electrode 25 are in blood and neither electrode is in contact with tissue. This adjustment is achieved when the ratio of the gain of sensor 130 to the gain of sensor 132 is proportional to the ratio of the area of tip electrode 24 to the area of reference electrode 25.

Figure 8A:
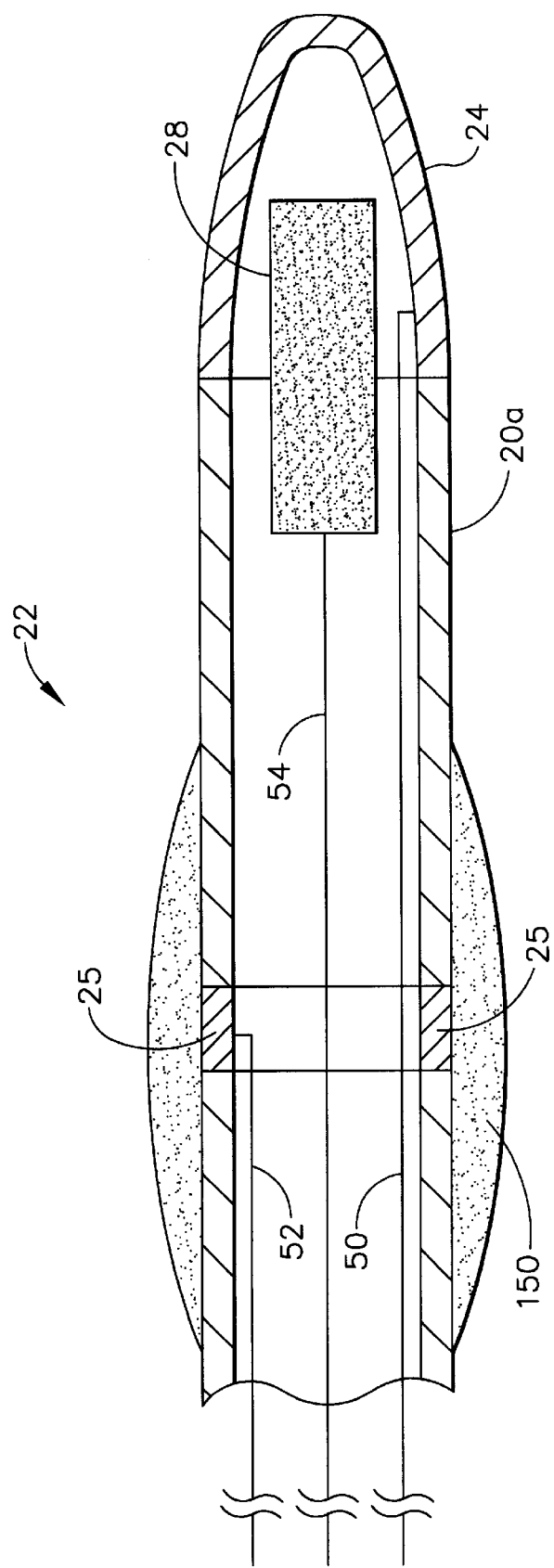
FIG. 8A is a cross-sectional view of a distal end of a catheter in which the reference electrode is protected from making contact with tissue by being covered with a membrane.
Figure 8B:
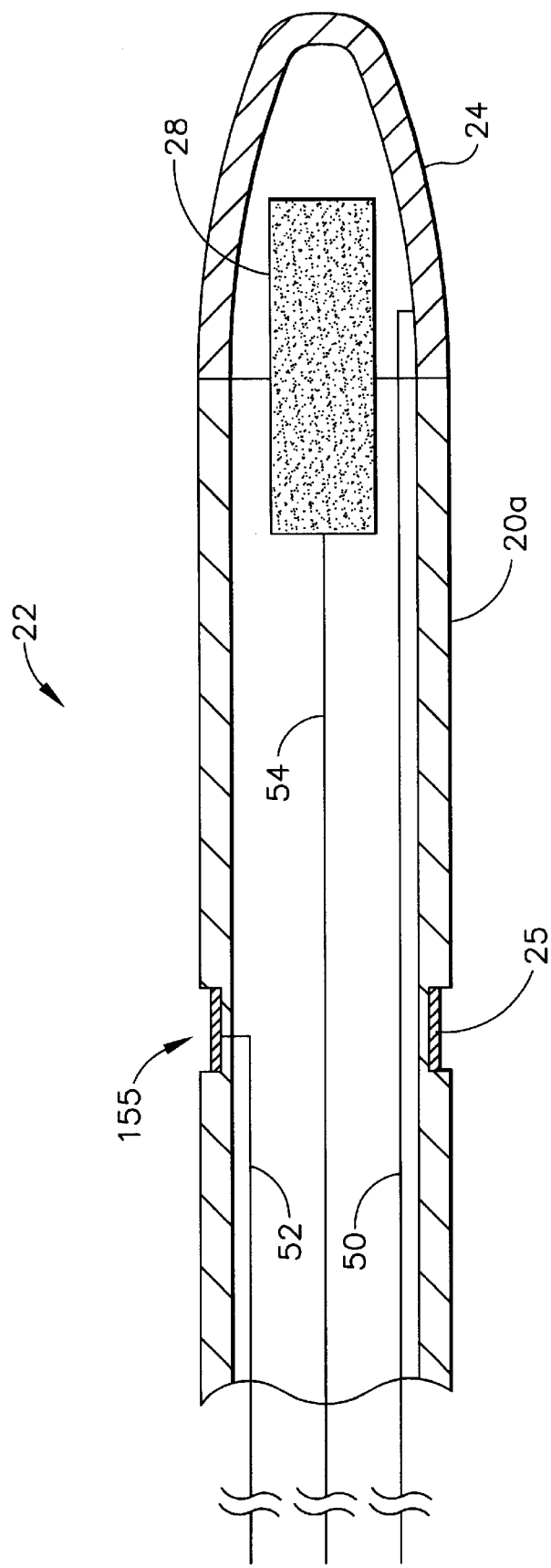
FIG. 8B is a cross-sectional view of a distal end of a catheter in which the reference electrode is protected from making contact with tissue by being recessed in the catheter body.

Reference electrode 25 is preferably protected from making contact with tissue. One manner of protecting reference electrode 25 from contacting tissue is to cover reference electrode 25 with a porous or semi-permeable membrane 150 (FIG. 8A). The membrane 150, in the form of a sleeve covering the reference electrode 25, permits contact of the reference electrode 25 with blood but prevents contact with tissue. The catheter body 20a is made of a non-conducting, non-toxic material such as polyurethane, polyetherimide or polyetherether ketone (PEEK). Alternatively, as shown in FIG. 8B, the reference electrode 25 may be protected from contact with tissue by being contained in channel 155 on catheter body 20a. .

The method of the invention may be employed by introducing catheter 20 into the body through an incision of the vasculature. Catheter 20 is then advanced into or proximate to the tissue of interest, for example, into a chamber of the heart. In operation, the system and method of the invention of detecting electrode-tissue contact may be employed in an intermittent, or, preferably, in a continuous manner. Employed continuously during an electrophysiology mapping procedure, for example, the method of the invention may be employed while recording intracardiac electrograms with tip electrode 24. ECG signals are typically in the frequency range from about 0.05 Hz to about 500 Hz. In contrast, the contact-testing signals sent to tip electrode 24 by signal generator 56 or 90 are typically in the frequency range of about 10 kHz to about 100 kHz. The electrocardiogram information may be decoupled from the contact-testing signal by using a suitable band pass filter.

The system and method of the invention may be used in creating an electrical map of a chamber of a heart as disclosed in commonly assigned U.S. Pat. No. 5,546,951; U.S. patent application Ser. No. 08/793,371; and PCT application WO 96/05768, which are incorporated herein in their entirety by reference. They may also be used in the generation of a mechanical or electromechanical map of a chamber of a heart as disclosed in U.S. Pat. No. 5,738,096 which is incorporated herein in its entirety by reference. Employed in connection with an electrophysiology study, for example, for the generation of an electrical or electromechanical map of a chamber of a heart, data acquisition may be controlled so that location and electrical information are not acquired unless the tip electrode is determined to be in contact with tissue. Alternatively, if it is determined that some of the data are acquired under conditions in which the tip electrode is not in contact with tissue, such data may be afforded less weight (or, in the limit, no weight) in the resultant electrical or electromechanical map. Similarly, in a cardiac ablation procedure, the ablation power source may be interlocked with the contact detection system so that ablation energy is only supplied to the tip electrode when contact of the tip electrode with tissue is detected.

Figure 9A:
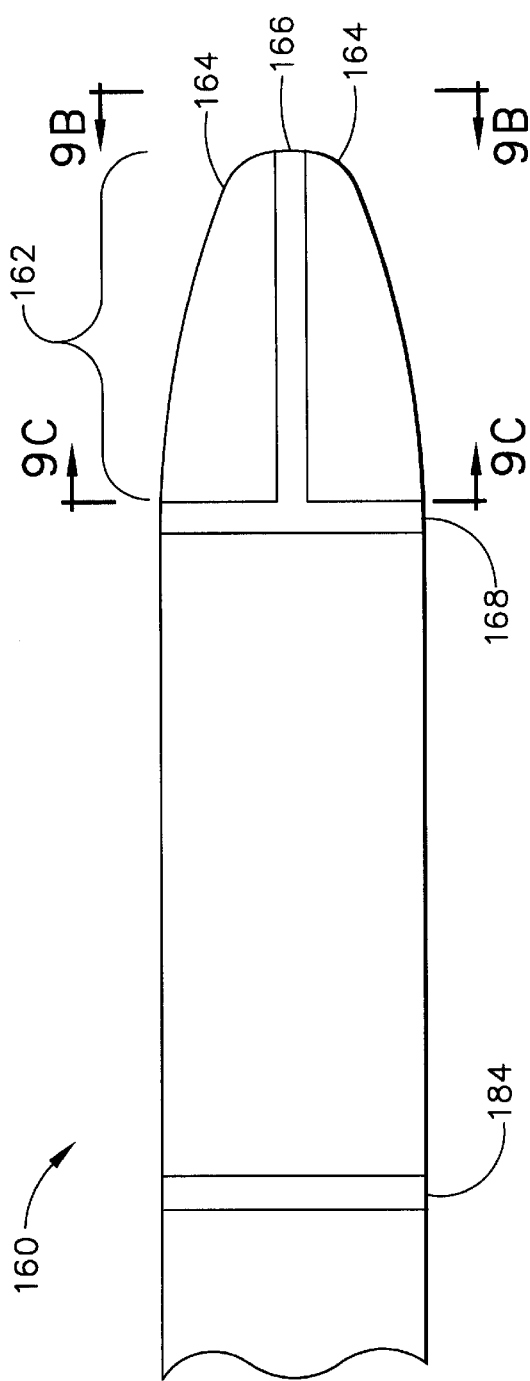
FIG. 9A is a top plan view of the distal end of a catheter with a split-tip design for use in the system and method of the invention.
Figure 9C:
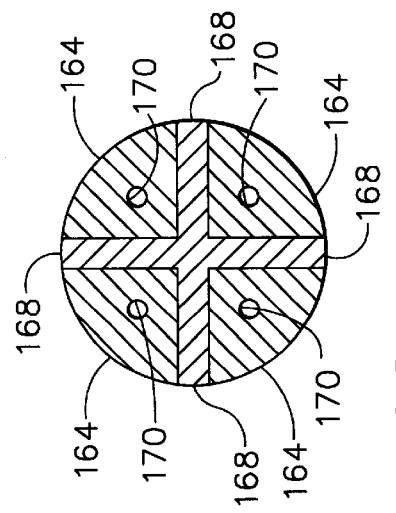
FIG. 9C is an end view of the proximal end of the electrode assembly of the catheter of FIG. 9A.
Figure 9B:
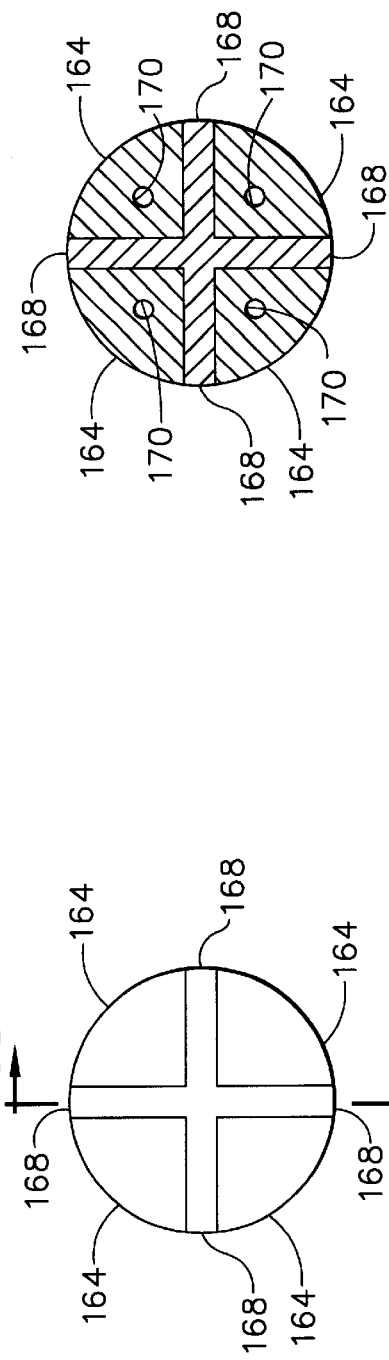
FIG. 9B is an end view of the distal tip of the catheter of FIG. 9A.
Figure 9D:
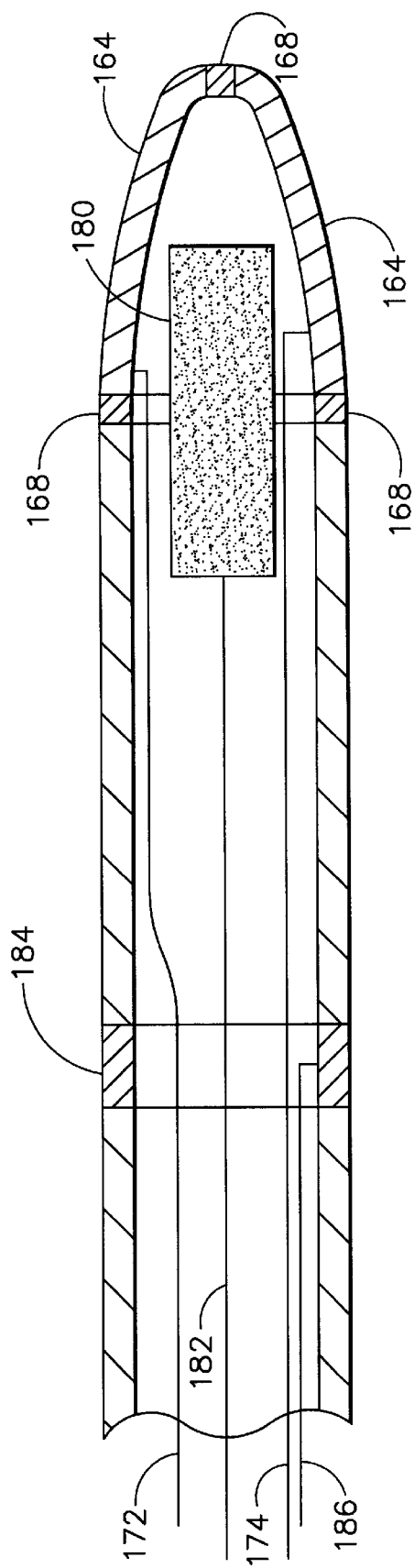
FIG. 9D is a view in longitudinal cross-section of the distal end of the catheter of FIG. 9A.

FIGS. 9A, 9B, 9C and 9D show an alternate distal end embodiment of the catheter 20 for use in the system and method of the invention. Catheter 20 has a distal end 160 which comprises a distal tip electrode assembly 162. Distal tip electrode assembly 162 comprises a plurality of individual distal tip electrodes 164 at distal tip 166. Each individual distal tip electrode 164 in electrode assembly 162 is electrically insulated from the other individual distal tip electrodes by non-conductor 168, which may be comprised of a material such as polyurethane, for example. Each individual distal tip electrode 164 has a lead bore hole 170 in which a lead is soldered for communication with the control and data acquisition circuitry. Thus, in this embodiment, the catheter 20 includes four leads for connection with the four individual distal tip electrodes (two of the four leads, 172 and 174, are shown in FIG. 9D). Distal end 160 of catheter 20 also comprises a location sensor 180 which is connected to signal processing circuits 40 via lead 182, as well as reference electrode 184 which communicates with signal processing circuits 40 via lead 186.

In the embodiment shown in FIGS. 9A through 9D, electrode assembly 162 comprises four individual distal tip electrodes 164 at four distinct quadrants. Alternatively, the electrode assembly at catheter distal tip 166 may comprise fewer or greater than four individual distal tip electrodes.

Figure 10:
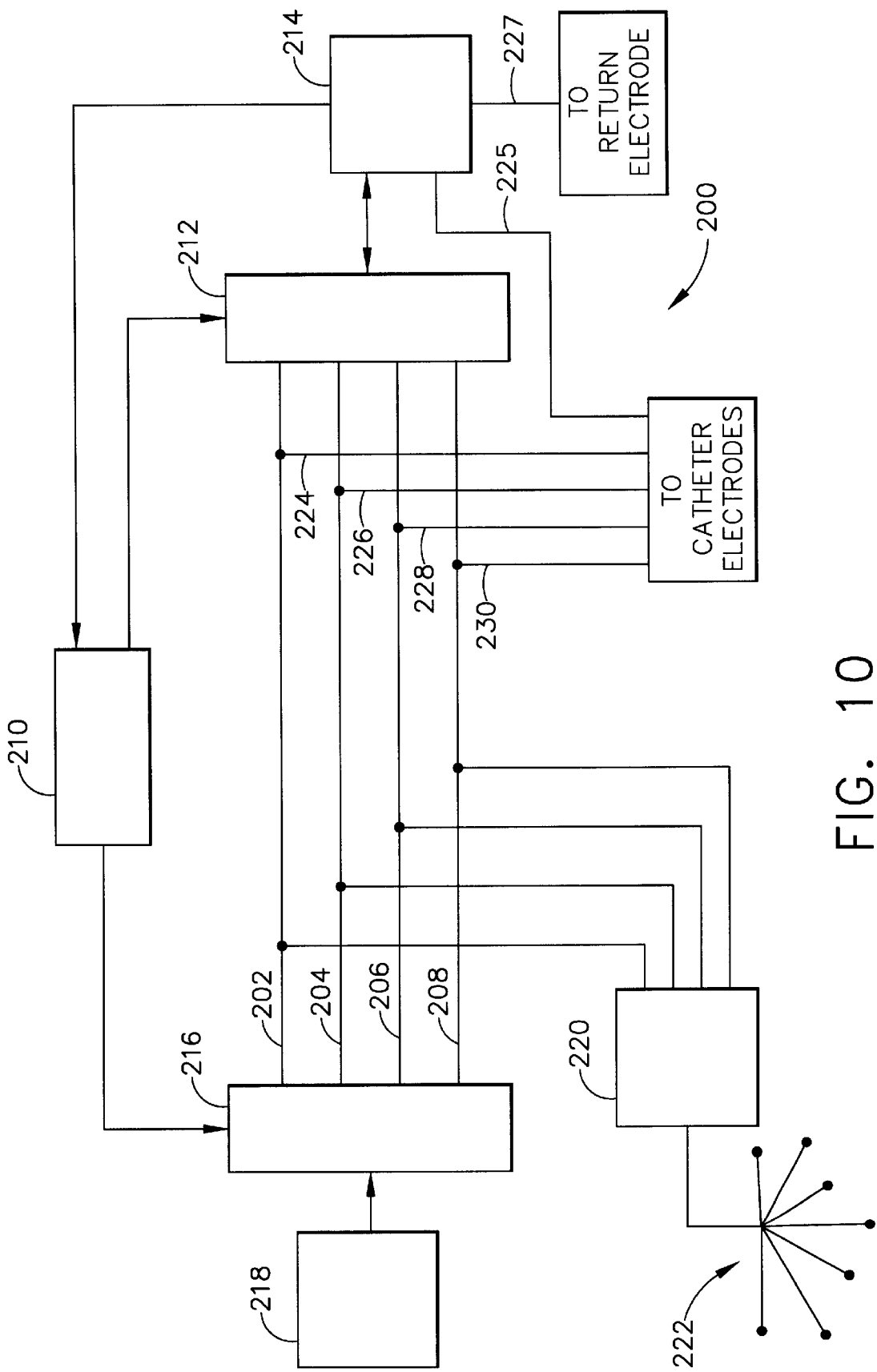
FIG. 10 is a schematic diagram showing a system for mapping the electrical activity of a chamber of a heart and for ablation of sites within the chamber.

The catheter of FIGS. 9A through 9D may be used with any of the contact measuring circuits shown in FIGS. 3 through 7. As shown in FIG. 10, a system 200 is used for mapping the electrical activity of a chamber of a heart and for performing therapeutic ablation using a multi-electrode catheter of the type shown in FIGS. 9A–9D and a contact detecting circuit of the type shown in FIGS. 3–7. System 200 consists of four channels 202, 204, 206 and 208. Each channel is in communication with one of the individual distal tip electrodes 164 on distal end 160 of catheter 20 via leads 224, 226, 228 and 230. Operating in a first mode, controller 210 commands multiplexer 212 to switch between channels 202 through 208 to permit differential impedance measurements across each of the individual tip electrodes 164 and the return electrode 48 by contact detection circuit 214. In addition to communicating with the individual tip electrodes 164 via multiplexer 212, contact detection circuit 214 communicates with reference electrode 184 via lead 225 and with return electrode 48 via lead 227. Contact detection circuit 214 may contain any of the circuitry shown in FIGS. 3 through 7. The signal generator associated with contact detection circuit 214 sequentially sends a contact detection signal through multiplexer 212 to each of the distal tip electrodes 164. Differential signals are measured across each of the individual tip electrodes 164 and the return electrode 48, and these differential signals are compared by contact detection circuit 214 to the differential signals across reference electrode 184 to the return electrode 48. Detection of tissue contact by each individual tip electrode 164 is accomplished as hereinabove described. Operating in a second mode, controller 210 commands multiplexer 216 to selectively close switching circuits and to permit ablation energy to flow from ablation power source 218 to those electrodes 164 determined in the first mode to be in contact with tissue. Thus, the system 200 selectively ablates at each selected tip electrode 164, i.e. only at those tip electrodes 164 that are in contact with tissue.

System 200 also contains electrocardiogram (ECG) monitoring and recording circuitry 220 to permit monitoring and recording of electrograms from each distal tip electrode 164. ECG circuitry 220 also contains provisions for monitoring and recording external body contact electrograms from external body surface leads 222.

Figure 11:
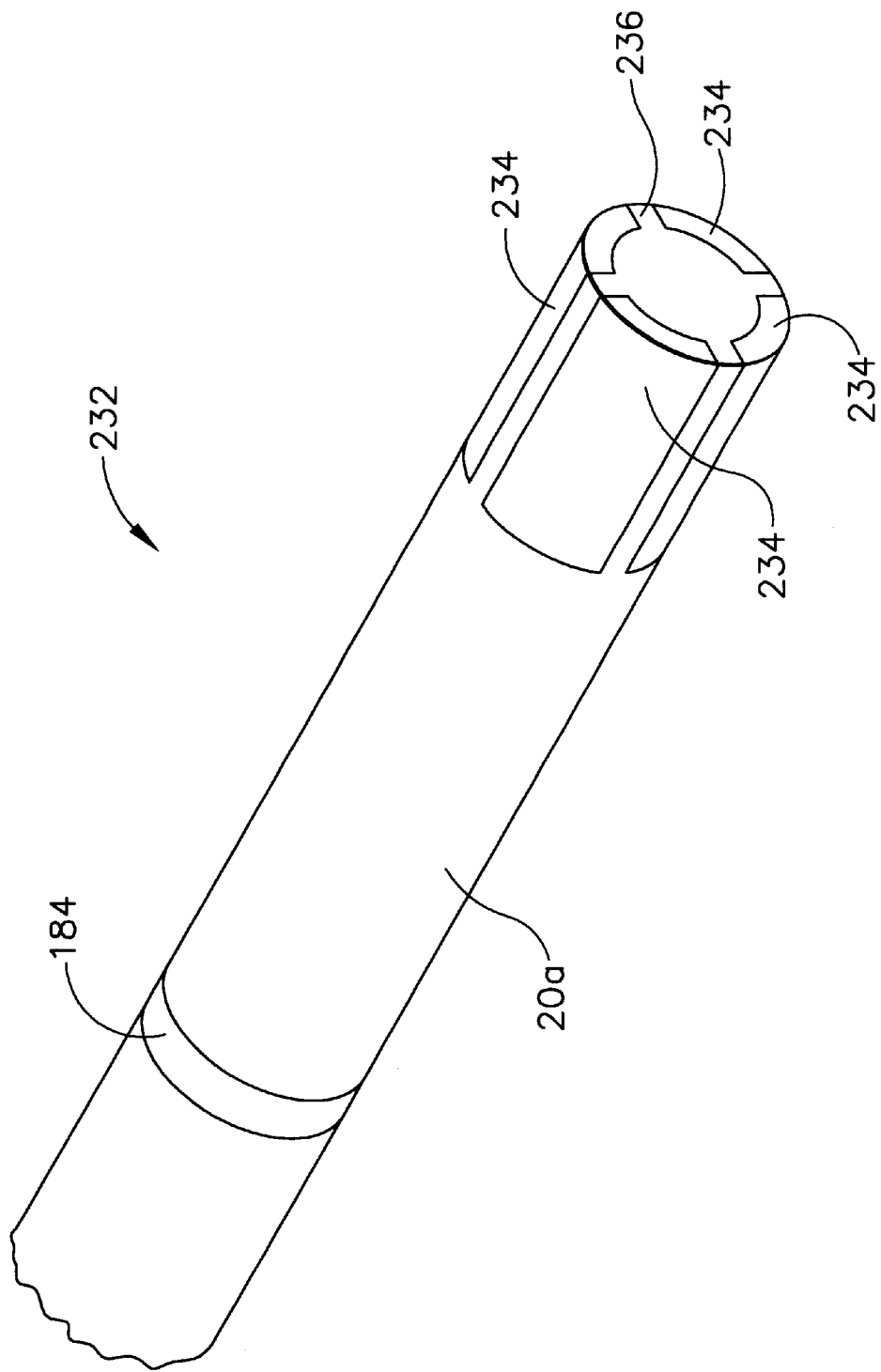
FIG. 11 is a perspective view of a distal end of a catheter having an alternative split-tip catheter design for use in practicing the system and method of the invention.

FIG. 11 shows another alternative embodiment of a distal end 232 of the catheter 20 containing a segmented distal tip electrode 236 for use in the system and method of the invention. As with the catheter of FIGS. 9A–9D, the catheter distal tip 236 contains four individual distal tip electrodes 234 equiangularly spaced about the circumference of catheter distal tip 236. Each electrode 234 has a portion located on the distal tip of distal end 232 and a longitudinally extending portion oriented along the longitudinal axis of the body 20a of the catheter distal end 232. Each distal tip electrode 234 is electrically insulated from the other electrodes by an insulating material such as polyurethane. Each distal tip electrode 234 is about 1.0 mm wide and from about 2 to about 8 mm long, and is connected via leads (not shown) to signal processing circuits 40. In addition, distal end 232 of catheter 20 contains a reference electrode 184. Each distal tip electrode 234 selectively ablates tissue based on impedance measurement in a manner as described above.

Figure 12:
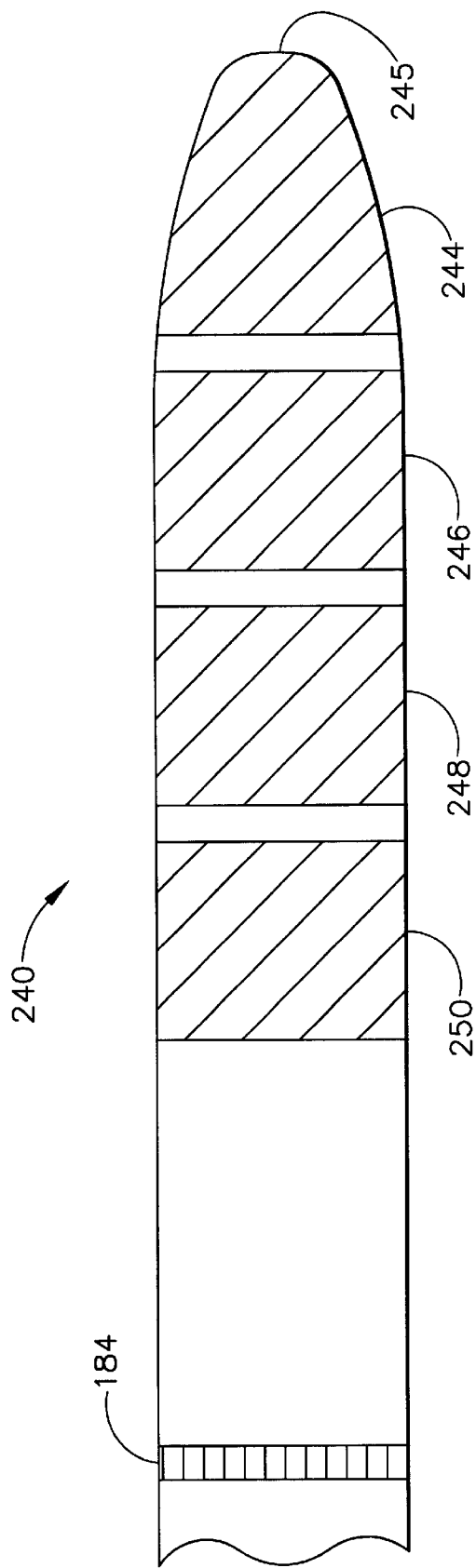
FIG. 12 is a cross-sectional view of the distal end of another embodiment of a catheter for use in the system and method of the invention.

FIG. 12 shows the distal end 240 of another embodiment of the catheter 20 that may be used in the system and method of the invention. The distal end 240 of the catheter 20 has a tip electrode 244 at distal tip 245 and ring electrodes 246, 248 and 250 spaced longitudinally from distal tip 245. Ring electrodes 246, 248 and 250 are each from about 3 to about 6 mm in length and are separated by an insulated area having an inter-electrode spacing distance of about 2 mm. Catheter 242 further preferably comprises a location sensor of the type previously described (not shown). Catheter 20 of FIG. 12 may be used with system 200 of FIG. 10 in cardiac mapping and ablation as hereinabove described. Catheter 242 is especially useful in generating a "line of block" in cardiac tissue by first detecting contact of each of electrodes 244, 246, 248 and 250 with tissue, and then either simultaneously or sequentially supplying RF energy to each of the electrodes determined to be in contact with tissue for providing selective ablation.

The catheter embodiment 20 of FIG. 12 is shown with three ring electrodes. Alternatively, distal end 240 of catheter 20 may contain fewer than or greater than three ring electrodes. The number of channels in system 200 should at least equal the number of electrodes contained on the catheter used in conjunction with the system.

Each of the electrodes in the multi-electrode embodiments shown in FIGS. 9A–9D, 11 and 12 may be equipped with a thermocouple for monitoring of electrode temperature and control of energy delivery to the electrodes during the selective ablation.

It will be appreciated that the preferred embodiments described above are cited by way of example and the full scope of the invention is limited only by the claims which follow.

What is claimed is:

1. A system for detecting contact of an electrode with tissue, said system comprising:
   a) a catheter comprising:
      i) a body having a proximal end and a distal end, said distal end having a distal tip;
      ii) a contact electrode adapted for contact with tissue, wherein said contact electrode is positioned at said catheter distal tip;
      iii) a location sensor for determining a position of said distal end;
   b) a reference electrode, wherein said reference electrode is positioned on said catheter;
   c) a return electrode, said return electrode functioning as a sink for said test signals to said distal tip electrode and to said reference electrode; and
   d) a contact detection circuit comprising:
      i) a signal generator for sending test signals to said contact electrode and to said reference electrode; and
      ii) a circuit to measure a differential electrical response to said test signals, said differential electrical response being indicative of contact of said contact electrode with tissue; wherein said circuit to measure a differential electrical response to said test signals comprises:
         (a) a first differential amplifier to measure a first electrical difference signal between said distal tip electrode and said return electrode; and
         (b) a second differential amplifier to measure a second electrical difference signal between said reference electrode and said return electrode.

2. The system of claim 1 wherein said location sensor is an electromagnetic location sensor.

3. The system of claim 1 wherein said reference electrode is protected from making contact with tissue.

4. The system of claim 3 wherein said reference electrode is protected by a membrane covering said electrode, said membrane permitting contact of said reference electrode with blood but not permitting contact of said reference electrode with tissue.

5. The system of claim 3 wherein said reference electrode is recessed relative to said catheter body.

6. The system of claim 1 wherein said return electrode is adapted for positioning internal to the body.

7. The system of claim 6 wherein said return electrode is positioned on said catheter.

8. The system of claim 1 wherein said return electrode is adapted for contact skin external to the body.

9. The system of claim 1 wherein said return electrode is dedicated for measuring differential signals with said distal tip electrode and with said reference electrode.

10. The system of claim 1 wherein said return electrode is connected to isolated ground.

11. The system of claim 1 wherein said return electrode is connected to an electrocardiogram device isolated ground.

12. The system of claim 1 wherein said distal tip electrode and said reference electrode are supplied with a first constant current and second constant current, respectively, said first constant current being equal to said second constant current.

13. The system of claim 12 wherein said return electrode is driven with a third constant current, said third current being opposite in phase with said first constant current and said second constant current.

14. The system of claim 1 which further comprises a third differential amplifier to measure an electrical difference signal between said first differential signal and said second differential signal.

15. The system of claim 14 wherein said first differential amplifier measures a first voltage difference between said distal tip electrode and said return electrode, said second differential amplifier measures a second voltage difference between said reference electrode and said return electrode, and said third differential amplifier measures a voltage difference between said first voltage and said second voltage.

16. The system of claim 14 wherein said electrical difference signal measured by said third differential amplifier is rectified by a synchronous detector.

17. The system of claim 1 wherein said tip electrode and said reference electrode have a first area and a second area, respectively, and said first amplifier and said second amplifier have a first gain and a second gain, respectively, said first gain to said second gain being proportional to said first area to said second area.

18. The system of claim 1 wherein said location sensor is an electromagnetic location sensor.

19. The system of claim 1 wherein said circuit to measure a differential electrical response to said test signals comprises a bridge circuit, said bridge circuit comprising a first resistive element and a second resistive element, said resistive elements each having a first side and a second side, said first side of said first resistive element connected with said first side of said second resistive element, said second side of said first resistive element connected with said reference electrode, said second side of said second resistive element connected with said distal tip electrode, said bridge having a first input between said first resistive element and said second resistive element and a second input connected to said return electrode, and a first output between said first resistive element and said reference electrode and a second output between said second resistive element and said distal tip electrode.

20. The system of claim 19 wherein said first resistive element is a first resistor and said second resistive element is a second resistor.

21. The system of claim 20 wherein said first resistor has a first resistance and said second resistor has a second resistance, and wherein said tip electrode has a tip electrode area and said reference electrode has a reference electrode area, said first resistance to said second resistance being proportional to said tip electrode area to said reference electrode area.

22. The system of claim 19 wherein said first resistive element is a first high output impedance buffer and said second resistive element is a second high output impedance buffer.

23. The system of claim 22 wherein said first high output impedance buffer has a first output current, said second high output buffer has a second output current, and wherein said tip electrode has a tip electrode area and said reference electrode has a reference electrode area, said first output current to said second output current being proportional to said tip electrode area to said reference electrode area.

24. The system of claim 19 wherein said bridge outputs are connected to a differential amplifier, said differential amplifier measuring a bridge output voltage indicative of contact of said distal tip electrode with tissue.

25. The system of claim 24 wherein said differential amplifier has an output that is rectified by a synchronous detector.

26. The system of claim 19 wherein said location sensor is an electromagnetic location sensor.

27. The system of claim 1 wherein said circuit to measure a differential electrical response to said test signals comprises a first current sensor for measuring current to said reference electrode and a second current sensor for measuring current to said distal tip electrode.

28. The system of claim 27 wherein said current sensors are selected from current transformers and Hall effect sensors.

29. The system of claim 27 wherein said first current sensor has a first gain and said second current sensor has a second gain, said distal tip electrode has a tip electrode area and said reference electrode has a reference electrode area, said first gain to said second gain being proportional to said tip electrode area to said reference electrode area.

30. The system of claim 27 wherein said first current sensor and said second current sensor have outputs connected to a differential amplifier, said amplifier measuring a voltage indicative of contact of said distal tip electrode with tissue.

31. The system of claim 30 wherein said differential amplifier has an output rectified by a synchronous detector.

32. The system of claim 27 wherein said location sensor is an electromagnetic location sensor.

33. A method of detecting contact of an electrode with tissue, said method comprising the steps of:
   a) providing a catheter comprising
      i) a body having a proximal end and a distal end, said distal end having a distal tip;
      ii) a contact electrode adapted for contact with tissue, wherein said contact electrode is positioned at said catheter distal tip;
      iii) a location sensor for determining a position of said distal end;
   b) providing a reference electrode, wherein said reference electrode is positioned on said catheter;
   c) providing test signals to said contact electrode and to said reference electrode;
   d) measuring a differential electrical response to said test signals, wherein said differential electrical response is indicative of contact of said contact electrode with tissue by:
      i) measuring a first electrical difference signal between said distal tip electrode and a return electrode and a second electrical difference signal between said reference electrode and said return electrode; and
      ii) comparing said first electrical difference signal with said second electrical difference signal to detect contact of said distal tip electrode with tissue.

34. The method of claim 33 wherein said location sensor is an electromagnetic location sensor.

35. The method of claim 33 wherein said reference electrode is protected from making contact with tissue.

36. The method of claim 35 wherein said reference electrode is protected by a membrane covering said electrode, said membrane permitting contact of said reference electrode with blood but not permitting contact of said reference electrode with tissue.

37. The method of claim 35 wherein said reference electrode is recessed relative to said catheter body.

38. The method of claim 33 wherein said test signals provided to said distal tip and reference electrodes are constant current signals.

39. The method of claim 33 wherein comparing said first electrical difference signal with said second electrical difference signal comprises feeding said first electrical difference signal and said second electrical difference signal to a differential amplifier to produce a third electrical difference signal indicative of contact of said distal tip electrode with tissue.

40. The method of claim 39 wherein said first and said second electrical difference signals are adjusted to provide a null difference signal from said differential amplifier when said distal tip electrode and said reference electrode are both in blood and neither electrode is in contact with tissue.

41. The method of claim 33 wherein said location sensor is an electromagnetic location sensor.

42. The method of claim 33 wherein measuring a differential electrical response to said test signals comprises:
   a) providing a bridge circuit comprising a first resistive element and a second resistive element, said resistive elements each having a first side and a second side, said first side of said first resistive element connected with said first side of said second resistive-element, said second side of said first resistive element connected with said reference electrode, said second side of said second resistive element connected with said distal tip electrode, said bridge having a first input between said first resistive element and said second resistive element and a second resistive element and a second input connected to said return electrode, and a first output between said first resistive element and said reference electrode and a second output between said second resistive element and said distal tip electrode; and
   b) measuring a signal across said bridge outputs to detect contact of said distal tip electrode with tissue.

43. The method of claim 42 wherein said first resistive element comprises a first resistor and said second resistive element comprises a second resistor.

44. The method of claim 42 wherein said first resistive element comprises a first high output impedance buffer and said second resistive element comprises a second high output impedance buffer.

45. The method of claim 42 wherein said signal across said bridge outputs is measured with a differential amplifier.

46. The method of claim 45 wherein said signal across said bridge outputs is adjusted to provide a null signal from said differential amplifier when said distal tip electrode and said reference electrode are both in blood and neither electrode is in contact with tissue.

47. The method of claim 42 wherein said location sensor is an electromagnetic sensor.

48. The method of claim 33 wherein measuring a differential electrical response to said test signals comprises measuring current to said reference electrode with a first current sensor and measuring current to said distal tip electrode with a second current sensor, said first current sensor and said second current sensor having outputs connected to a differential amplifier, said amplifier measuring a voltage indicative of contact of said distal tip electrode with tissue.

49. The method of claim 48 wherein said current sensors are selected from current transformers and Hall effect sensors.

50. The method of claim 48 wherein said current sensors have output signals, said signals being adjusted to provide a null signal from said differential amplifier when said distal tip electrode and said reference electrode are both in blood and neither electrode is in contact with tissue.

51. The method of claim 48 wherein said location sensor is an electromagnetic location sensor.

52. The method of claim 33 wherein measuring a differential electrical response to said test signals comprises:
   a) measuring a first impedance between said distal tip electrode and a return electrode and a second impedance between said reference electrode and said return electrode; and
   b) comparing said first and second impedances to detect contact of said catheter distal tip electrode with tissue.

53. The method of claim 52 wherein said location sensor is an electromagnetic location sensor.

54. The method of claim 53 which further comprises delivering ablation energy to said distal tip electrode in accordance with said distal tip electrode being in contact with tissue.

55. A method of detecting contact of an electrode with tissue, said method comprising the steps of:
   a) providing a catheter comprising:
      i) a body having a proximal end and a distal end, said distal end having a distal tip;
      ii) a contact electrode adapted for contact with tissue, wherein said contact electrode is positioned at said catheter distal tip; and
      iii) a location sensor for determining a position of said distal end;
   b) providing a reference electrode, wherein said reference electrode is positioned on said catheter;
   c) providing test signals to said contact electrode and to said reference electrode;
   d) measuring a differential electrical response to said test signals, said differential electrical response being indicative of contact of said contact electrode with tissue;
   e) collecting electrical information from said distal tip electrode and location information from said location sensor at a plurality of points on said tissue; and
   f) generating an electrical map of said tissue from said electrical and location information, said electrical and location information at each of said points being weighted in said map in accordance with contact being detected between said distal tip electrode and said tissue at said points.

56. A method of detecting contact of an electrode with tissue, said method comprising the steps of:
   a) providing a catheter comprising:
      i) a body having a proximal end and a distal end, said distal end having a distal tip;
      ii) a contact electrode adapted for contact with tissue, wherein said contact electrode is positioned at said catheter distal tip; and
      iii) a location sensor for determining a position of said distal end;
   b) providing a reference electrode, wherein said reference electrode is positioned on said catheter;
   c) providing test signals to said contact electrode and to said reference electrode;
   d) measuring a differential electrical response to said test signals, said differential electrical response being indicative of contact of said contact electrode with tissue;
   e) collecting electrical information from said distal tip electrode and mechanical information from said location sensor at a plurality of points on said tissue; and
   f) generating an electromechanical map of said tissue from said electrical and mechanical information, said electrical and mechanical information at each of said points being weighted in said map in accordance with contact being detected between said distal tip electrode and said tissue at said points.

57. The method of claim 56 which further comprises delivering ablation energy to said distal tip electrode in accordance with said distal tip electrode being in contact with tissue.

* * * * *